(12) United States Patent
Gomtsyan et al.

(10) Patent No.: US 7,504,520 B2
(45) Date of Patent: Mar. 17, 2009

(54) ANTAGONISTS OF THE VANILLOID RECEPTOR SUBTYPE 1 (VR1) AND USE THEREOF

(75) Inventors: Arthur Gomtsyan, Vernon Hills, IL (US); Richard J. Perner, Gurnee, IL (US); John R. Koenig, Chicago, IL (US); Margaret Chi-Ping Hsu, Lake Forest, IL (US); Dilinie P. Fernando, Lake Forest, IL (US); Chih-Hung Lee, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 199 days.

(21) Appl. No.: 11/431,459

(22) Filed: May 10, 2006

(65) Prior Publication Data

US 2006/0281799 A1    Dec. 14, 2006

Related U.S. Application Data

(60) Provisional application No. 60/679,708, filed on May 11, 2005.

(51) Int. Cl.
*C07D 209/04* (2006.01)
*C07D 421/00* (2006.01)
*C07D 277/00* (2006.01)
*C07D 295/00* (2006.01)
*C07D 409/00* (2006.01)
*C07D 207/46* (2006.01)

(52) U.S. Cl. .......... 548/469; 548/100; 548/125; 548/146; 548/190; 548/215; 548/233; 548/400; 548/416; 548/452; 548/465; 548/527; 548/577

(58) Field of Classification Search ........... 548/146, 548/215, 300.1, 100, 125, 190, 233, 400, 548/416, 452, 465, 469, 527, 577
See application file for complete search history.

(56) References Cited

FOREIGN PATENT DOCUMENTS

WO    WO 2004/110350    * 12/2004

OTHER PUBLICATIONS

Wolff, Burger's Medicinal Chemistry, 5th Ed., vol. 1, pp. 975-977, 1994.*

Caterina, M.J., et al., "Impaired Nociception and Pain Sensation in Mice Lacking the capsaicin Receptor", Science, vol. 288, pp. 306-313 (2000).

Davis, J., et al., "Vanilloid receptor-1 is essential for inflammatory thermal hyperalgesia", Nature, vol. 405, pp. 183-187.

Fowler, C., "Intravesical Treatment of Overactive Bladder", Urology, vol. 55, Supp 5A, pp. 60-64 (2000).

Nolano, M., et al., "Topical capsaicin in humans: parallel loss of epidermal nerve fibers and pain sensation", Pain, vol. 81, pp. 135-145 (1999).

Pircio, et al., "A New Method for the Evaluation of Analgesic Activity Using Adjuvant-Induced Arthritis in the Rat", Eur J. Pharmacol., vol. 31(2), pp. 207-215 (1975).

Rasmussen and Bowadt, "Ketene Chemistry 2. A General Procedure for the Synthesis of 2-Alkoxycyclopropane-carboxylic Esters and Acids Starting from Aldehydes and Ketene", Synthesis, p. 114-117 (1989).

* cited by examiner

*Primary Examiner*—Kamal A Saeed
*Assistant Examiner*—Samantha L Shterengarts
(74) *Attorney, Agent, or Firm*—Sonali S. Srivastava

(57) ABSTRACT

The present invention is directed to compounds of formula (I)

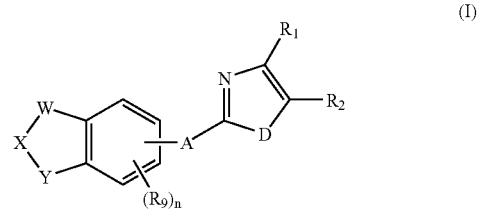

wherein variables W, X, Y, D, A, n, $R_1$, $R_2$ and $R_9$ are as defined in the description.

51 Claims, No Drawings

ANTAGONISTS OF THE VANILLOID RECEPTOR SUBTYPE 1 (VR1) AND USE THEREOF

This application claims priority to U.S. Provisional Application Ser. No. 60/679,708 filed on May 11, 2005.

FIELD OF INVENTION

The present invention relates to compounds of formula (I), which are useful for treating disorders caused by or exacerbated by vanilloid receptor activity. The present invention also includes pharmaceutical compositions containing compounds of formula (I) and methods for treating pain, bladder overactivity, and urinary incontinence using said compounds and said pharmaceutical compositions.

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel VR1 antagonists and have utility in treating pain, pain associated with inflammatory states, inflammatory thermal hyperalgesia, bladder overactivity, and urinary incontinence.

SUMMARY OF THE PRESENT INVENTION

The present invention discloses oxazolyl compounds, a method for inhibiting the VR1 receptor in mammals using these compounds, a method for controlling pain, pains states associated with inflammatoary states, inflammatory thermal hyperalgesia, bladder overactivity, and urinary incontinence, in mammals, and pharmaceutical compositions including those compounds. More particularly, the present invention is directed to compounds of formula (I)

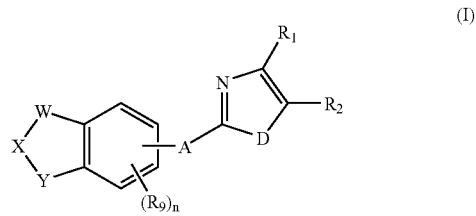

or a pharmaceutically acceptable salt, amide, ester, prodrug, or salt of a prodrug thereof, wherein A is O or —N($R_3$);

D is —N($R_4$), O or S;

$R_3$ and $R_4$ are each independently selected from the group consisting of hydrogen, alkyl, —C(O)alkyl, and —S(O)$_2$(alkyl);

$R_1$ and $R_2$ are each independently selected from the group consisting of hydrogen, alkyl alkenyl, cyano, nitro, halogen, —O$R_5$, —OC(O)$R_5$, —S$R_5$, —S(O)$_2R_5$, —S(O)$_2$O$R_5$, —S(O)$_2$N($R_5$)($R_6$), —N($R_5$)($R_6$), —N($R_6$)C(O)$R_5$, —N($R_6$)C(O)N($R_5$)($R_6$), —N($R_6$)S(O)$_2$N($R_5$)($R_6$), —C(O)$R_5$, —C(O)O$R_5$, —C(O)N($R_5$)($R_6$), haloalkyl, -alkylenyl-O$R_5$, -alkylenyl-OC(O)$R_5$, -alkylenyl-S$R_5$, -alkylenyl-S(O)$_2R_5$, -alkylenyl-S(O)$_2$O$R_5$, -alkylenyl-S(O)$_2$N($R_5$)($R_6$), -alkylenyl-N($R_5$)($R_6$), -alkylenyl-N($R_6$)C(O)$R_5$, -alkylenyl-N($R_6$)C(O)N($R_5$)($R_6$), -alkylenyl-N($R_6$)S(O)$_2$N($R_5$)($R_6$), -alkylenyl-C(O)$R_5$, -alkylenyl-C(O)O$R_5$, -alkylenyl-C(O)N($R_5$)($R_6$), —$R_7$, and -alkylenyl-$R_7$; provided that when one of $R_1$ and $R_2$ is hydrogen, the other is not hydrogen;

$R_5$ at each occurrence is independently selected from the group consisting of hydrogen, alkyl, alkenyl, haloalkyl and benzyl;

$R_6$ at each occurrence is independently selected from the group consisting of hydrogen and alkyl;

$R_7$ at each occurrence is independently selected from the group consisting of cycloalkyl, cycloalkenyl, heterocycle, aryl and heteroaryl; wherein each $R_7$ is independently substituted with 0, 1, 2, 3, 4 or 5 substituents independently selected from the group consisting of alkyl, alkenyl, halogen, cyano, nitro, hydroxy, alkoxy, haloalkoxy, —S(alkyl), —S(O)$_2$(alkyl), —N(H)$_2$, —N(H)(alkyl), —N(alkyl)$_2$, —N(H)C(O)alkyl, —C(O)OH, —C(O)Oalkyl, —C(O)NH$_2$, —C(O)N(H)alkyl, —C(O)N(alkyl)$_2$, —R$_8$, cyanoalkyl, haloalkyl, hydroxyalkyl, alkoxyalkyl, haloalkoxyalkyl, -alkylenyl-S(alkyl), -alkylenyl-S(O)$_2$(alkyl), -alkylenyl-N(H)$_2$, -alkylenyl-N(H)(alkyl), -alkylenyl-N(alkyl)$_2$, -alkylenyl-N(H)C(O)alkyl, -alkylenyl-C(O)OH, -alkylenyl-C(O)Oalkyl, -alkylenyl-C(O)NH$_2$, -alkylenyl-C(O)N(H)alkyl, -alkylenyl-C(O)N(alkyl)$_2$, and -alkylenyl-R$_8$;

R$_8$ at each occurrence is independently selected from the group consisting of cycloalkyl, cycloalkenyl, heterocycle, aryl and heteroaryl; wherein each R$_8$ is independently substituted with 0, 1, 2, 3, 4 or 5 substituents independently selected from the group consisting of alkyl, alkenyl, halogen, cyano, nitro, hydroxy, alkoxy, haloalkoxy, —S(alkyl), —S(O)$_2$(alkyl), —N(H)$_2$, —N(H)(alkyl), —N(alkyl)$_2$, —N(H)C(O)alkyl, —C(O)OH, —C(O)Oalkyl, —C(O)NH$_2$, —C(O)N(H)alkyl, —C(O)N(alkyl)$_2$, cyanoalkyl, haloalkyl, hydroxyalkyl, alkoxyalkyl, haloalkoxyalkyl, -alkylenyl-S(alkyl), -alkylenyl-S(O)$_2$(alkyl), -alkylenyl-N(H)$_2$, -alkylenyl-N(H)(alkyl), -alkylenyl-N(alkyl)$_2$, -alkylenyl-N(H)C(O)alkyl, -alkylenyl-C(O)OH, -alkylenyl-C(O)Oalkyl, -alkylenyl-C(O)NH$_2$, -alkylenyl-C(O)N(H)alkyl, and -alkylenyl-C(O)N(alkyl)$_2$;

W and Y are each independently selected from the group consisting of —C(R$_x$)(R$_y$)— and —N(R$_z$)—; provided that when one of W and Y is —N(R$_z$)—, then the other is —C(R$_x$)(R$_y$)—;

X is selected from the group consisting of —C(O)—, —C(R$_x$)(R$_y$)—, —N(R$_z$)—, —C(R$_x$)(R$_y$)—C(R$_x$)(R$_y$)—, —C(O)—C(R$_x$)(R$_y$)—, —C(R$_x$)(R$_y$)—C(O)—, —C(R$_x$)(R$_y$)—N(R$_z$)— and —N(R$_z$)—C(R$_x$)(R$_y$)—; provide that when one of W and Y is —N(R$_z$)—, then X is selected from the group consisting of —C(R$_x$)(R$_y$)— and —C(R$_x$)(R$_y$)—C(R$_x$)(R$_y$)—;

R$_x$ and R$_y$ at each occurrence are each independently selected from the group consisting of hydrogen, alkyl, haloalkyl, —OR$_a$, —OC(O)R$_a$, —SR$_a$, —S(O)$_2$R$_a$, —S(O)$_2$N(R$_a$)(R$_b$), —S(O)$_2$OR$_a$, —N(R$_a$)(R$_b$), —N(R$_b$)C(O)R$_a$, —N(R$_b$)C(O)N(R$_a$)(R$_b$), —N(R$_b$)S(O)$_2$N(R$_a$)(R$_b$), —C(O)OR$_a$, —C(O)R$_a$, —C(O)N(R$_a$)(R$_b$), -alkylenyl-OR$_a$, -alkylenyl-OC(O)R$_a$, -alkylenyl-SR$_a$, -alkylenyl-S(O)$_2$R$_a$, -alkylenyl-S(O)$_2$N(R$_a$)(R$_b$), -alkylenyl-S(O)$_2$OR$_a$, -alkylenyl-N(R$_a$)(R$_b$), -alkylenyl-N(R$_b$)C(O)R$_a$, -alkylenyl-N(R$_b$)C(O)N(R$_a$)(R$_b$), -alkylenyl-N(R$_b$)S(O)$_2$N(R$_a$)(R$_b$), -alkylenyl-C(O)OR$_a$, -alkylenyl-C(O)R$_a$, -alkylenyl-C(O)N(R$_a$)(R$_b$), —R$_8$ and -alkylenyl-R$_8$;

R$_a$ at each occurrence is independently selected from the group consisting of hydrogen, alkyl, haloalkyl, —R$_8$ and -alkylenyl-R$_8$;

R$_b$ at each occurrence is independently selected from the group consisting of hydrogen, alkyl and haloalkyl; alternatively, R$_a$ and R$_b$ together with the nitrogen atom to which they are attached form a heterocycle ring substituted with 0, 1, 2, 3, 4 or 5 substituents independently selected from the group consisting of halogen, alkyl and haloalkyl;

R$_z$ at each occurrence is independently selected from the group consisting of hydrogen, alkyl, —C(O)alkyl, and —S(O)$_2$(alkyl);

R$_9$ at each occurrence is independently selected from the group consisting of halogen, alkyl, haloalkyl, hydroxyalkyl, alkoxyalkyl and haloalkoxyalkyl; and n is 0, 1, 2, or 3.

DETAILED DESCRIPTION OF THE INVENTION

Definition of Terms

As used throughout this specification and the appended claims, the following terms have the following meanings:

The term "alkenyl" as used herein, means a straight or branched chain hydrocarbon containing from 2 to 10 carbon atoms and at least one carbon-carbon double bond. Examples of alkenyl include, but not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylenyl" or "alkylene" as used herein, means a divalent group derived from a straight or branched chain hydrocarbon of from 1 to 10 carbon atoms. Representative examples of alkylene or alkylenyl include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but not limited to, methoxymethyl, methoxyethyl, and ethoxyethyl.

The term "aryl" as used herein, means a phenyl group, or a bicyclic or a tricyclic hydrocarbon fused ring system containing zero heteroatom wherein one or more of the fused rings is a phenyl group. Bicyclic hydrocarbon fused ring systems are exemplified by a phenyl group fused to a monocyclic cycloalkyl group, as defined herein, a monocyclic cycloalkenyl group, as defined herein, or another phenyl group. Tricyclic hydrocarbon fused ring systems are exemplified by the bicyclic fused hydrocarbon ring system as defined hereinabove, fused to a monocyclic cycloalkyl group, as defined herein, a monocyclic cycloalkenyl group, as defined herein, or another phenyl group. The aryl groups of the present invention are appended to the parent moiety through any substitutable atoms in the group. The aryl groups of the present invention can be unsubstituted or substituted. Representative examples of aryl include, but are not limited to, phenyl, anthracenyl, naphthyl, fluorenyl, 2,3-dihydro-1H-inden-1-yl, 2,3-dihydro-1H-inden-4-yl, inden-1-yl, inden-4-yl, naphthyl, phenyl, 5,6,7,8-tetrahydronaphthalen-1-yl, 1,2,3,4-tetrahydronaphthalen-2-yl and tetrahydronaphthyl.

The term "arylalkyl" as used herein, refers to an aryl group, as used herein, appended to the parent moiety through an alkyl group as defined herein.

The term "cyano" as used herein, refers to —CN.

The term "cyanoalkyl" as used herein, refers to an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, refers to a monocyclic, bicyclic or tricyclic saturated hydrocarbon ring system having zero heteroatom. The monocyclic ring system has three to eight carbon atoms and zero heteroatom. Examples of monocyclic ring systems include cyclopropyl, cyclobutyl, cyclopentyl, cyclohexyl, cycloheptyl, and cyclooctyl. The monocyclic cycloalkyl of the present invention may contain one or two bridges. The term "bridge" refers to a connection between two of the non-adjacent carbon atoms connected by an alkylene bridge between one and three additional carbon atoms. Representative examples of monocyclic cycloalky that contain such bridge or bridges include, but are not limited to, bicyclo[2.2.1]heptan-1-yl, bicyclo[2.2.1]heptan-2-yl, bicyclo[2.2.1]heptan-1-yl, bicyclo[3.1.1]heptan-6-yl, bicyclo[2.2.2]octan-1-yl and adamantyl. The term "cycloalkyl" of the present invention also include a bicyclic cycloalkyl or tricyclic cycloalkyl. The bicyclic cycloalkyl of the present invention refers to a monocyclic cycloalkyl ring fused to another monocyclic cycloalkyl group, as defined herein. Representative examples of the bicyclic cycloalkyl include, but are not limited to, 4a(2H) decahydronaphthalenyl. The bicyclic cycloalkyl groups of the present invention may have two of the non-adjacent carbon atoms connected by an alkylene bridge between one and three additional carbon atoms. Representative examples of the bicyclic cycloalkyl groups that contain such connection between two non-adjacent carbon atoms include, but not limited to, octahydro-2,5-methanopentalenyl. The tricyclic cycloalkyl group of the present invention refers to a bicyclic cycloalkyl ring, as defined hereinabove, fused to another monocyclic cycloalkyl group, as defined herein. Representative example of the tricyclic cycloalkyl group includes, but is not limited to, dodecahydro-1H-fluoren-9-yl. The monocyclic, bicyclic and tricyclic cycloalkyl groups of the present invention can be unsubstituted or substituted, and are connected to the parent molecula moiety through any substitutable carbon atom of the group.

The term "cycloalkenyl" or "cycloalkene" as used herein, refers to a non-aromatic, partially unsaturated, monocyclic or bicyclic hydrocarbon ring system having zero heteroatom. The monocyclic ring systems have 4, 5, 6, 7 or 8 carbon atoms and at least one carbon-carbon double bond. The 4-membered ring systems have one double bond, the 5- or 6-membered ring systems have one or two double bonds, and the 7- or 8-membered ring systems have one, two or three double bonds. Representative examples of cycloalkenyl groups include, but not limited to, cyclobutenyl, cyclopentenyl, cyclohexenyl, cycloheptenyl and cyclooctenyl. The term "cycloalkenyl" of the present invention also include a bicyclic fused ring system wherein the monocyclic cycloalkenyl ring is fused to a monocyclic cycloalkyl group, as defined herein, or another monocyclic cycloalkenyl group, as defined herein. Representative examples of the bicyclic cycloalkenyl groups include, but not limited to, 4,5,6,7-tetrahydro-3aH-indene, octahydronaphthalenyl and 1,6-dihydro-pentalene. The cycloalkenyl groups of the present invention can be unsubstituted or substituted, and are attached to the parent molecular moiety through any substitutable carbon atom of the group.

The term "halo" or "halogen" as used herein, means —Cl, —Br, —I or —F.

The term "haloalkoxy" as used herein, refers to an alkoxy group, as defined herein, in which one, two, three, four, five or six hydrogen atoms are replaced by halogen. Representative examples of haloalkoxy include, but not limited to, chloromethoxy, 2-fluoroethoxy, trifluoromethoxy, hexafluoroethoxy, 2-chloro-3-fluoropentyloxy, and pentafluoroethoxy.

The term "haloalkoxyalkyl" as used herein, refers to a haloalkoxy group, as defined herein, appended to the parent molecular moiety through an alkyl group, as defined herein. Examples of haloalkoxyalkyl include, but not limited to, trifluoromethoxymethyl.

The term "haloalkyl" as used herein, refers to an alkyl group, as defined herein, in which one, two, three or four, five or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, refers to a monocyclic or bicyclic, non-aromatic, saturated or partially unsaturated ring system. Monocyclic ring systems are exemplified by a 4-membered ring containing one heteroatom independently selected from oxygen, nitrogen and sulfur; or a 5-, 6-, 7-, or 8-membered ring containing one, two or three heteroatoms wherein the heteroatoms are independently selected from nitrogen, oxygen and sulfur. The 5-membered ring has 0 or 1 double bond. The 6-memebered ring has 0, 1 or 2 double bonds. The 7- or 8-membered ring has 0, 1, 2 or 3 double bonds. Representative examples of monocyclic ring systems include, but are not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include but are not limited to, benzodioxinyl, benzodioxolyl, benzopyranyl, benzothiopyranyl, 2,3-dihydroindolyl, indolizinyl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic or bicyclic ring systems as defined herein may have two of the non-adjacent carbon atoms connected by a heteroatom selected from nitrogen, oxygen or sulfur, or by an alkylene bridge of between one and three additional carbon atoms. Representative examples of monocyclic or bicyclic ring systems that contain such connection between two non-adjacent carbon atoms include, but not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 8-azabicyclo[3.2.1]oct-8-yl, 3-oxa-8-azabicyclo[3.2.1]octyl, 1,4-diazabicyclo[3.2.2]nonyl, 3,10-diazabicyclo[4.3.1]decyl, or 8-oxa-3-azabicyclo[3.2.1]octyl, octahydro-1H-4,7-methanoisoindolyl, and octahydro-1H-4,7-epoxyisoindolyl. The heterocycle groups of the invention are substituted or unsubstituted, and are connected to the parent molecular moiety through any substitutable carbon or nitrogen atom in the groups. The nitrogen heteroatom may or may not be quaternized, and the nitrogen or sulfur heteroatom may or may not be oxidized. In addition, the nitrogen containing heterocyclic rings may or may not be N-protected.

The term "heteroaryl" as used herein, refers to monocyclic or bicyclic aromatic ring systems where at least one atom is selected from the group consisting of N, O, and S, and the remaining atoms are carbon. The monocyclic heteroaryl groups have five or six-membered rings containing at least one heteroatom selected from N, O or S and the remainings are carbon. The five membered rings have two double bonds, and the six membered rings have three double bonds. The term "heteroaryl" also includes bicyclic heteroaryl groups where the monocyclic heteroaryl ring, as defined herein, is fused to a phenyl group, a monocyclic cycloalkyl group, as defined herein, a monocyclic cycloalkenyl group, as defined herein, a monocyclic heterocycle group, as defined herein, or an additional monocyclic heteroaryl group. Representative examples of the monocyclic and bicyclic heteroaryl groups include, but not limited to, benzothienyl, benzoxazolyl, benzimidazolyl, benzoxadiazolyl, 6,7-dihydro-1,3-benzothiazolyl, furyl, imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienyl, triazolyl, thiadiazolyl, tetrazolyl, 1,2,3,4-tetrahydro-1,8-naphthyridin-2-yl, and 5,6,7,8-tetrahydroquinolin-5-yl. The heteroaryl groups of the present invention can be substituted or unsubstituted, and are connected to the parent molecular moiety through any substitutable carbon or nitrogen atom in the groups. In addition, the nitrogen heteroatom may or may not be quaternized, the nitrogen and the sulfur atoms in the group may or may not be oxidized. Also, the nitrogen containing rings may or may not be N-protected.

The term "heteroatom" as used herein, refers to nitrogen, oxygen or sulfur atom.

The term "hydroxy" or "hydroxyl" as used herein, means an —OH group.

The term "hydroxyalkyl" as used herein, refers to an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means —$NO_2$.

Compounds of the Present Invention

2. Compounds of the invention can have the formula (I) as described above. More particularly, compounds of formula (I) can include, but are not limited to compounds wherein D is —$N(R_4)$ and A is O. Compounds of the invention can include those wherein D is —$N(R_4)$ and A is —$N(R_3)$ Other compounds of the invention include those in which A is O and D is S.( ) Other compounds included in the present invention may be those in which D is S and A is —$N(R_3)$. Preferred compounds are those in which D is S and A is —$N(R_3)$, $R_1$ is hydrogen; $R_2$ is —$R_7$; $R_3$ is hydrogen; $R_7$ is phenyl; W is —$C(R_x)(R_y)$; Y is —$C(R_x)(R_y)$; X is —$C(R_x)(R_y)$—$C(R_x)(R_y)$—; $R_x$ is —$O(R_a)$, and $R_y$ is hydrogen. Other compounds of the present invention comprise those in which both D and A are O. Compounds of the invention can include those wherein D is O, A is —$N(R_3)$, wherein $R_3$ is hydrogen Preferred compounds are those in which D is O, A is —$N(R_3)$, $R_3$ is hydrogen, $R_1$ is hydrogen and $R_2$ is aryl,) more preferably those in which $R_2$ is phenyl. These preferred compounds include those in which W is —$C(R_x)(R_y)$, Y is —$C(R_x)(R_y)$, and X is —$C(O)$—$C(R_x)(R_y)$—, wherein $R_x$ and $R_y$ are hydrogen Other compounds comprised are those in which $R_2$ is phenyl, W is —$C(R_x)(R_y)$, Y is —$C(R_x)(R_y)$, and X is —$C(R_x)(R_y)$—$C(R_x)(R_y)$—; preferably those in which $R_x$ is —OH and $R_y$ is hydrogen. Also, preferred compounds include those in which $R_x$ is —$N(R_a)(R_b)$, and $R_a$ and $R_b$ are hydrogen. and those in which $R_x$ is —$N(R_a)(R_b)$, $R_a$ is —$S(O)_2$(alkyl), and $R_b$ is hydrogen.

Other compounds of the present invention include those in which D is O, A is —$N(R_3)$, wherein $R_3$ is hydrogen, $R_1$ is hydrogen, and $R_2$ is cycloalkyl. Preferably those in which W is —$C(R_x)(R_y)$, Y is —$C(R_x)(R_y)$, and X is —$C(O)$—$C(R_x)(R_y)$—, wherein $R_x$ and $R_y$ are hydrogen. Other compounds include those in which D is O, A is —$N(R_3)$, wherein $R_3$ is hydrogen, $R_1$ is hydrogen, $R_2$ is cycloalkyl, W is —$C(R_x)(R_y)$, Y is —$C(R_x)(R_y)$, and X is —$C(R_x)(R_y)$—$C(R_x)(R_y)$—, preferably those in which $R_x$ is —OH and $R_y$ is hydrogen. Other compounds of the present invention include those in which D is O, A is —$N(R_3)$, wherein $R_3$ is hydrogen, $R_1$ is hydrogen, and $R_2$ is alkyl, preferably those in which W is —$C(R_x)(R_y)$, Y is —$C(R_x)(R_y)$, and X is —$C(O)$—$C(R_x)(R_y)$—, wherein $R_x$ and $R_y$ are hydrogen Other preferred compounds include those in which D is O, A is —$N(R_3)$, wherein $R_3$ is hydrogen, $R_1$ is hydrogen, $R_2$ is alkyl, W is —$C(R_x)(R_y)$, Y is —$C(R_x)(R_y)$, and X is —$C(R_x)(R_y)$—$C(R_x)(R_y)$—, preferably those in which $R_x$ is —OH and $R_y$ is hydrogen. The present invention also includes compounds in which D is O, A is —$N(R_3)$, wherein $R_3$ is hydrogen, $R_1$ is hydrogen, $R_2$ is alkyl-$R_7$. Preferred compounds are those in which $R_7$ is phenyl, W is —$C(R_x)(R_y)$, Y is —$C(R_x)(R_y)$, and X is —$C(O)$—$C(R_x)(R_y)$—, wherein $R_x$ and $R_y$ are hydrogen. Other compounds included in the present invention are those in which D is O, A is —$N(R_3)$, wherein $R_3$ is hydrogen, $R_1$ is hydrogen, $R_2$ is alkyl-$R_7$, $R_7$ is phenyl, W is —$C(R_x)(R_y)$, Y is —$C(R_x)(R_y)$, and X is —$C(R_x)(R_y)$—$C(R_x)(R_y)$—, preferably those in which $R_x$ is —OH and $R_y$ is hydrogen. The present invention also includes compounds wherein D is O, A is —$N(R_3)$, $R_3$ is alkyl, W is —$C(R_x)(R_y)$, Y is —$C(R_x)(R_y)$, and X is —$C(O)$—$C(R_x)(R_y)$—, wherein $R_x$ and $R_y$ are hydrogen. Other included compounds are those in which D is O, A is —$N(R_3)$, $R_3$ is —$C(O)$alkyl, W is —$C(R_x)(R_y)$, Y is —$C(R_x)(R_y)$, and X is —$C(O)$—$C(R_x)(R_y)$—, wherein $R_x$ and $R_y$ are hydrogen, and those in which D is O, A is —$N(R_3)$, $R_3$ is —$C(O)$alkyl, W is —$C(R_x)(R_y)$, Y is —$C(R_x)(R_y)$, and X is —$C(R_x)(R_y)$—$C(R_x)(R_y)$—, preferably those in which $R_x$ is —OH and $R_y$ is hydrogen. The present invention also includes pharmaceutical compositions comprising therapeutically effective amounts of a compound with a formula (I) as described above, or a pharmaceutically acceptable salt, amide, ester or prodrug thereof.

Preparation of Compounds of the Present Invention

The compounds of this invention can be prepared by a variety of synthetic procedures. Representative procedures are shown in, but are not limited to, Schemes 1-5.

Scheme 1

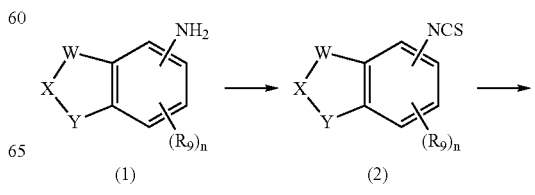

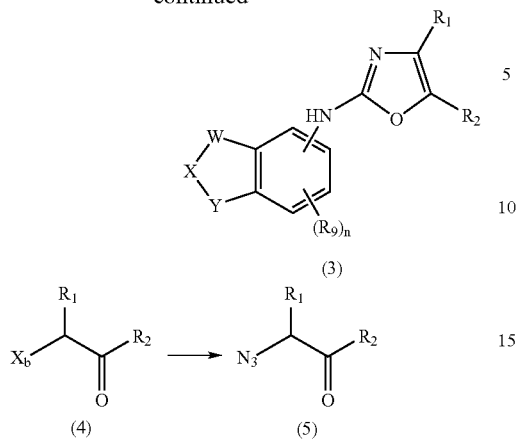

(3)

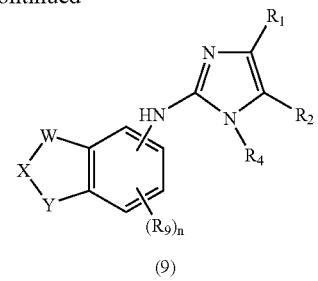

(9)

Imidazoles of formula (9) wherein $R_1$, $R_2$, $R_9$, n, W, X, Y and $R_4$ are as defined in formula (I) can be prepared as shown in Scheme 2. Amines of formula (1) can be converted to guanidines of formula (8) using a reagent such as, but not limited to, nitrosoguanidine/HCl, cyanamide/HCl or reagent of formula (6) wherein $R_{101}$ is tert-butoxycarbonyl or benzyloxycarbonyl. In the case of where reagents of formula (6) is used, deprotection of the guanidine using methodologies known to one skilled in organic synthesis, transforms compounds of formula (7) wherein $R_{102}$ is is tert-butoxycarbonyl or benzyloxycarbonyl to compounds of formula (7) wherein $R_{102}$ is hydrogen. Reaction of guanidines of formula (7) wherein $R_{102}$ is hydrogen with compounds of formula (8) wherein $X_a$ is a leaving group such as, but not limited to, Cl, Br, I, triflate or methanesulfonate, (prepared from the corresponding alcohols using synthetic routes known to one skilled in the art) followed by spontaneous ring closure, provides imidazoles of formula (9) wherein $R_4$ is hydrogen.

Imidazoles of formula (9) wherein $R_4$ is hydrogen can be converted to compounds of formula (9) wherein $R_4$ is alkyl by reaction with alkyl halides of formula $R_4X$ wherein X is Br, Cl or I in the presence of a base such as, but not limited to, sodium hydride.

Imidazoles of formula (9) wherein $R_4$ is hydrogen can be converted to compounds of formula (9) wherein $R_4$ is —C(O)alkyl by reaction with acyl halides of formula alkylC(O)X wherein X is Cl, Br or I, or anhydrides of formula $(R_4CO)_2O$ wherein $R_4$ is alkyl, in the presence of a base such as triethylamine.

Imidazoles of formula (9) wherein $R_4$ is hydrogen can be converted to compounds of formula (9) wherein $R_4$ is —S(O)$_2$ alkyl by reaction with compounds of formula alkylS(O)$_2$X wherein X is Cl, Br or I in the presence of a base such as triethylamine.

Compounds of formula (3) wherein W, X, Y, $R_1$, $R_2$, $R_9$ and n are as defined in formula (I) can be prepared as shown in Scheme 1. Amines of formula (1), either purchased or prepared using methodologies known to one skilled in the art, can be converted to isothiocyanates of formula (2) by reacting with reagents such as, but not limited to, O,O-dipyridin-2-yl-thiocarbonate, thiophosgene, thiourea/HCl or CS$_2$/aqueous NH$_3$. Reaction of the isothiocyanates of formula (2) with azides of formula (5), followed by spontaneous ring closure provides oxazoles of formula (3). The reaction is generally performed in the presence of triphenylphosphine or tributylphosphine in a solvent such as, but not limited to, dichloromethane or dioxane, at a temperature from about room temperature to about 100° C.

Azides of formula (5) can be purchased or prepared from compounds of formula (4) wherein $X_b$ is I, Cl, Br, mesylate or tosylate by reacting with sodium azide or trimethylsilylazide in a solvent such as, but not limited to, acetone, N,N-dimethylformamide, ethanol, dimethylsulfoxide, or hexamethylphosphoramide, at a temperature from about room temperature to about 100° C.

Scheme 2

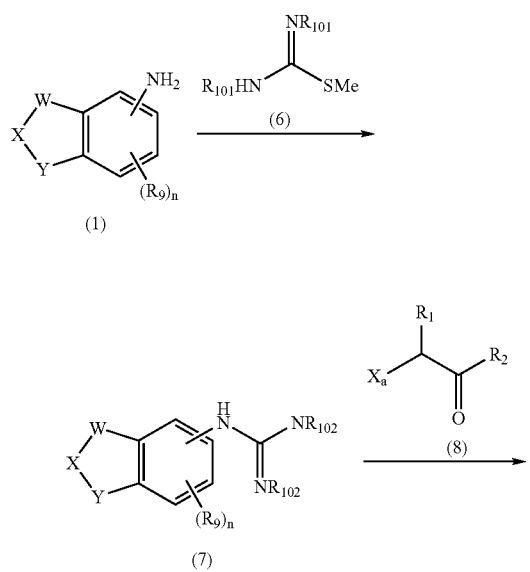

Scheme 3

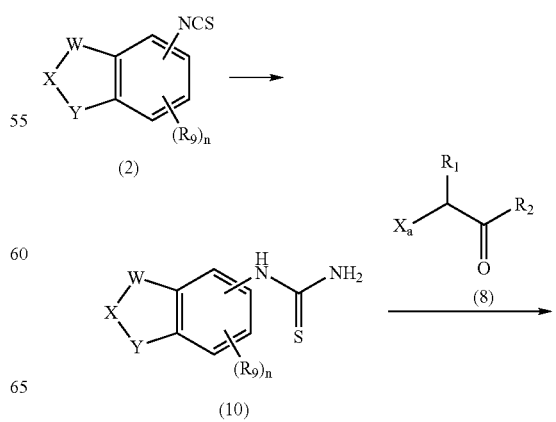

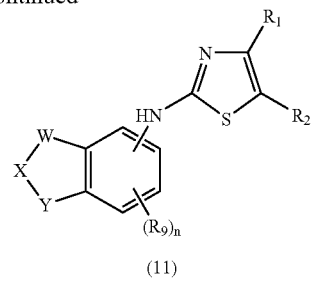

(11)

Thiazoles of formula (11) wherein W, X, Y, $R_1$, $R_2$, $R_9$ and n are as defined in formula (I), can be prepared from isothiocyanates of formula (2) as depicted in Scheme 3. Reaction of isothiocyanates of formula (2) with gaseous ammonia in a solvent such as, but not limited to, dioxane or tetrahydrofuran, at about room temperature provides thioureas of formula (10). Conversion of thioureas of formula (10) to thiazoles of formula (11) can be effected using similar reaction conditions employed for the transformation of compounds of formula (7) to imidazoles of formula (9).

Scheme 4

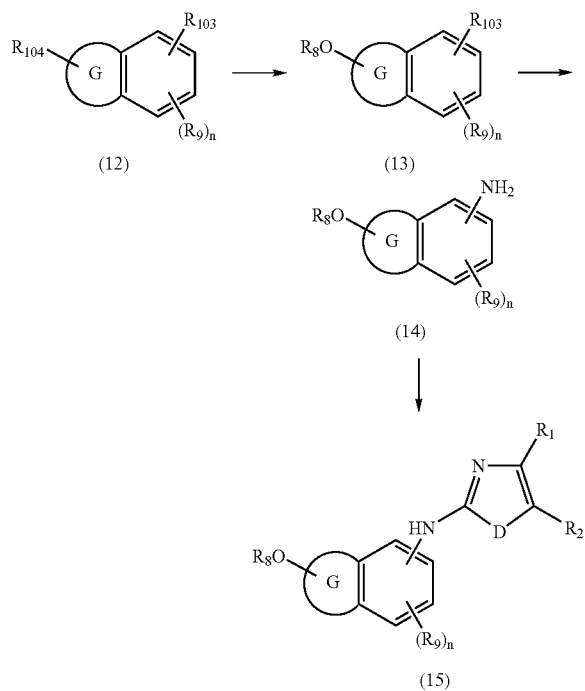

Compounds of formula (15) wherein D, $R_1$, $R_2$, $R_8$, $R_9$ and n are as defined in formula (I), and G is selected from the group consisting of cylclopentane, cyclohexane, piperidine and pyrrolidine, and each ring G is independently unsubstituted or substituted with substituents as described in —W—X—Y— of formula (I), can be prepared as shown in Scheme 4.

Alcohols of formula (12) wherein $R_{104}$ is —OH and $R_{103}$ is $NO_2$ or —N(H)($R_{105}$) wherein $R_{105}$ is a nitrogen protecting group, can be converted to compounds of formula (13) by reacting with compounds of formula $R_8X_c$ wherein $R_c$ is triflate, Br or I, in the presence of a metal catalyst, a ligand, and a base. The reaction is generally conducted in a solvent such as, but not limited to, dioxane, toluene, N,N-dimethylformamide (DMF), N,N-dimethylacetamide, N-methylpyrrolidinone (NMP) or pyridine. Examples of metal catalysts include, but not limited to, palladium diacetate and tris(dibenzylideneacetone)dipalladium(0). Examples of ligands include, but not limited to, 2,2'-bis(diphenylphosphino)-1,1'-binaphthyl and tri-tertbutylphosphine. Examples of bases include, but not limited to, sodium tert-butoxide, sodium hydride, and cesium carbonate.

Alternatively, compounds of formula (13) wherein $R_{103}$ is $NO_2$ or —N(H)($R_{105}$) and $R_{105}$ is a nitrogen protecting group can be made from the reaction of formula (12) wherein $R_{104}$ is triflate, Br or I, and $R_{103}$ is $NO_2$ or —N(H)($R_{105}$) wherein $R_{105}$ is a nitrogen protecting group, with alcohols of formula $R_8OH$ using the reaction conditions as described in the preceding paragraph.

Conversion of certain alcohols of formula (12) wherein $R_{104}$ is —OH and $R_{103}$ is $NO_2$ or —N(H)($R_{105}$) wherein $R_{105}$ is a nitrogen protecting group, to compounds of formula (13) can also be achieved by reaction with alcohols of formula $R_8OH$ in the presence of diethylazodicarboxylate or di-(tert-butyl)azodicarboxylate and triphenyl phosphine, a condition known as Mitsunobo reaction.

Subsequently, compounds of formula (13) wherein $R_{103}$ is N(H)($R_{105}$) and $R_{105}$ is a nitrogen protecting group can be converted to compounds of formula (14) by reaction with a suitable deprotecting reagent known to one skilled in the art. Compounds of formula (13) wherein $R_{103}$ is $NO_2$ can be reduced to compounds of formula (14) using a reducing agent. Examples of reducing agents include, but not limited to, lithium aluminium hydride or tin (or zinc or iron)/HCl. The transformation can also be effected by hydrogen in the presence of a catalyst, such as, but not limited to, palladium on carbon or palladium hydroxide on carbon.

Compounds of formula (14) can be converted to compounds of formula (15) using the reaction conditions as described in schemes 1, 2, and 3.

Scheme 5

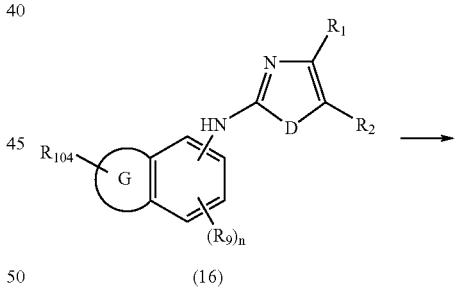

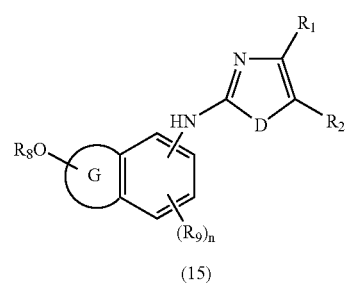

Alternatively, compounds of formula (15) wherein D, $R_1$, $R_2$, $R_8$, $R_9$ and n are as defined in formula (I), G is selected from the group consisting of cylclopentane, cyclohexane, piperidine and pyrrolidine and each G is independently unsubstituted or substituted with substituents as described in —W—X—Y— of formula (I), can be prepared from compounds of formula (16) wherein $R_{104}$ is halogen, triflate or —OH (either purchased or prepared using transformations as described in schemes 1, 2 and 3) using reaction conditions for the transformation of compounds of formula (12) to compounds of formula (13) as described in Scheme 4.

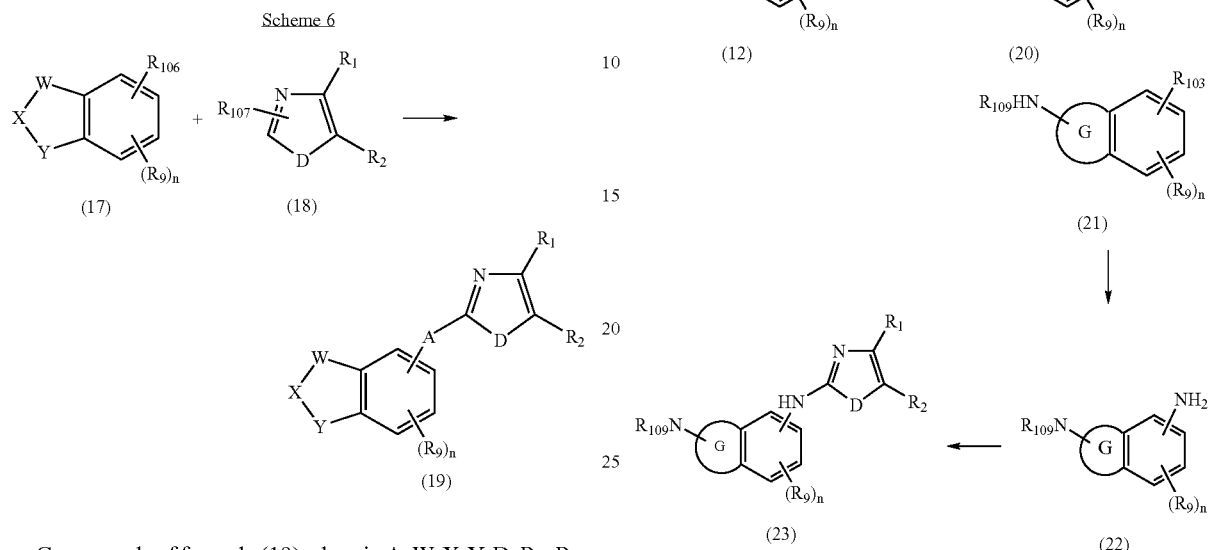

Compounds of formula (19) wherein A, W, X, Y, D, $R_1$, $R_2$, $R_9$ and n are as defined in formula (I), can be prepared as shown in Scheme 6.

Compounds of formula (17) wherein $R_{106}$ is triflate, Br or I, can be reacted with compounds of formula (18) wherein $R_{107}$ is $NH_2$ or OH, in the presence of a ligand, a metal catalyst and a base as shown in Scheme 4, to provide compounds of formula (19) wherein A is O or NH.

Alternatively, compounds of formula (17) wherein $R_{106}$ is $NH_2$ or OH, can be reacted with compounds of formula (18) wherein $R_{107}$ is triflate, Br or I, in the presence of a ligand, a metal catalyst and a base as shown in Scheme 4, to provide compounds of formula (19) wherein A is O or NH.

Compounds of formula (19) wherein A is O and W, X, Y, D, $R_1$, $R_2$, $R_9$ and n are as defined in formula (I), can also be obtained by reacting compounds of formula (17) wherein $R_{106}$ is OH with compounds of formula (18) wherein $R_{107}$ is OH using Mitsunobo conditions.

Compounds of formula (19) wherein A is NH can be converted to compounds of formula (19) wherein A is $N(R_3)$ wherein $R_3$ is alkyl, —C(O)alkyl or —S(O)$_2$(alkyl) can be achieved by reaction with compounds of formula $R_3X$ wherein X is Cl, Br or I and $R_3$ is alkyl, —C(O)alkyl or —S(O)$_2$(alkyl) as described in Scheme 2.

Compounds of formula (19) wherein W, X and Y together with the carbon atoms form a ring selected from the group consisting of cyclohexane and piperidine and that each ring is independently unsubstituted or substituted with substituents as described in W—X—Y of formula (I) can be either purchased or prepared by known synthetic routes. One example of such synthesis involves reduction of compounds of formula (19) wherein W, X and Y together with the carbon atoms form an unsubstituted or substituted ring selected from the group consisting of benzene and pyridine, using hydrogen gas, in the presence of Raney/nickel and sodium hydroxide.

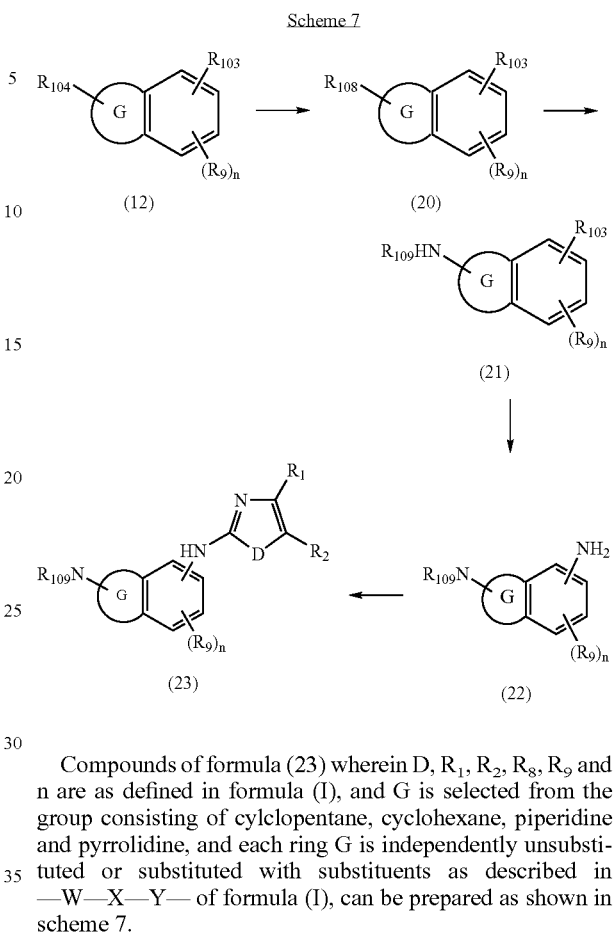

Compounds of formula (23) wherein D, $R_1$, $R_2$, $R_8$, $R_9$ and n are as defined in formula (I), and G is selected from the group consisting of cylclopentane, cyclohexane, piperidine and pyrrolidine, and each ring G is independently unsubstituted or substituted with substituents as described in —W—X—Y— of formula (I), can be prepared as shown in scheme 7.

Conversion of certain alcohols of formula (12), wherein $R_{104}$ is —OH and $R_{103}$ is $NO_2$ or —N(H)($R_{105}$) wherein $R_{105}$ is a nitrogen protecting group, to compounds of formula (20), wherein $R_{108}$ is a "protected" form of amine such as azido or phthlimido, can be achieved by activation of the hydroxyl group through conversion to, for example, a tosylate or mesylate group followed by reaction with a nitrogen source such as sodium azide or sodium phthalimide as in the Gabriel synthesis. Compounds of formula (20) can be converted to compounds of formula (21), wherein $R_{109}$ is hydrogen or a nitrogen protecting group, through a reduction and protection sequence known to one skilled in the art. Examples of reducing agents include, but not limited to, lithium aluminum hydride, hydrazine, and hydrogen in the presence of a catalyst. Compounds of formula (22) can be converted to compounds of formula (23) using the reaction conditions as described in schemes 1, 2, and 3.

It is understood that the schemes described herein are for illustrative purposes and that routine experimentation, including appropriate manipulation of the sequence of the synthetic route, protection of any chemical functionality that are not compatible with the reaction conditions and the removal of such protecting groups are included in the scope of the invention.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for ameliorating or preventing disorders involving VR1 receptor activation such as, but not limited to, inflammatory thermal hyperalgesia, bladder overactivity, and urinary incontinence as described by Nolano, M. et al., *Pain Vol.* 81, pages 135-145, (1999); Caterina, M. J. and Julius, D., *Annu. Rev. Neurosci. Vol.* 24, pages 487-517 (2001); Caterina, M. J. et al., *Science Vol.* 288 pages 306-313 (2000); Caterina, M. J. et al., *Nature Vol.* 389 pages 816-824 (1997); Fowler, C. *Urology Vol.* 55 pages 60-64 (2000); and Davis, J. et al., *Nature Vol.* 405 pages 183-187.

The present invention also provides pharmaceutical compositions that comprise compounds of the present invention. The pharmaceutical compositions comprise compounds of the present invention that may be formulated together with one or more non-toxic pharmaceutically acceptable carriers.

EXAMPLES

The following Examples are intended as an illustration of and not a limitation upon the scope of the invention as defined in the appended claims.

Example 1

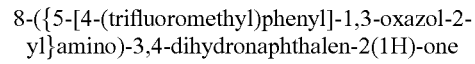
8-({5-[4-(trifluoromethyl)phenyl]-1,3-oxazol-2-yl}amino)-3,4-dihydronaphthalen-2(1H)-one Example 1A

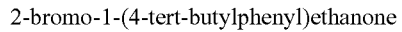
2-bromo-1-(4-tert-butylphenyl)ethanone

A solution of 4-tert-butylacetophenone (5 g, 28.4 mmol) in acetic acid (2 mL) was carefully (the reaction was exothermic) treated with $Br_2$ (1.46 mL, 28.5 mmol), followed by 48% aq. HBr (0.015 mL, 0.132 mmol). The reaction was stirred at room temperature for 4 hours, then was poured onto ice and was extracted with diethyl ether. The organic phase was concentrated and was then chromatographed on silica gel, eluting with 5% ethyl acetate-hexane, followed by 10% ethyl acetate-hexane, to afford the title compound as a pale brown oil, 1.305 g (18%). $^1$H NMR (DMSO-$d_6$) δ 7.94 (d, 2H, J=8.5 Hz), 7.58 (d, 2H, J=8.5 Hz), 4.90 (s, 2H), 1.31 (s, 9H); MS (ESI$^+$) m/z 255 (M+H).

Example 1B

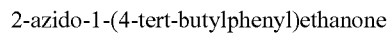
2-azido-1-(4-tert-butylphenyl)ethanone

To a solution of the product of Example 1A (985 mg, 3.86 mmol) in 45 mL acetone was added $NaN_3$ (0.505 g, 7.07 mmol), and the mixture stirred overnight at room temperature. The reaction mixture was poured into saturated NaCl solution and extracted with dichloromethane. The extracts were washed with saturated NaCl solution, dried over $Na_2SO_4$, and concentrated in vacuo to afford the title compound as a yellow oil (715 mg, 85%). $^1$H NMR (DMSO-$d_6$) δ

7.88 (d, 2H, J=8.5 Hz), 7.57 (d, 2H, J=8.5 Hz), 4.86 (s, 2H), 1.31 (s, 9H); MS (ESI$^+$) m/z 218 (M+H).

Example 1C tert-butyl 7-ethoxy-1-naphthylcarbamate

To 8-amino-2-naphthol (10 g, 62.9 mmol) in 200 mL tetrahydrofuran was added di-tert-butyl dicarbonate (13.4 g, 62.8 mmol) in 20 mL tetrahydrofuran, and the reaction mixture was refluxed overnight. The reaction mixture was cooled to room temperature and concentrated in vacuo. The residue was dissolved in ethyl acetate, washed with saturated $Na_2CO_3$ solution and water, dried over $Na_2SO_4$, filtered and concentrated. A solution of the concentrate in N,N-dimethylformamide (60 mL) was treated with $Cs_2CO_3$ (32.2 g, 98.8 mmol) and iodoethane (4.4 mL, 8.46 g, 53.5 mmol), and the mixture was vigorously stirred at 60° for 3 h. The mixture was then cooled to rt, poured into $H_2O$, and extracted with ethyl acetate. The extracts were washed with $H_2O$ and brine, dried over $MgSO_4$, filtered, and evaporated in vacuo to afford the title compound as a brown oil (14.47 g, 80%). $^1$H NMR (DMSO-$d_6$) δ 9.14 (s, 1H), 7.81 (d, 1H, 8.9 Hz), 7.61 (d, 1H, J=8.2 Hz), 7.54 (d, 1H, 7.8 Hz), 7.37 (d, 1H, J=2.7 Hz), 7.28 (t, 1H, J=7.8 Hz), 7.15 (dd, 1H, J=8.9 Hz, 2.7 Hz), 4.16 (q, 2H, J=7.1 Hz), 1.50 (s, 9H), 1.09 (t, 3H, J=7.0 Hz); MS (ESI$^+$) m/z 310 (M+Na)$^+$.

Example 1D 7-ethoxy-1-naphthylamine

To a solution of the product of Example 1C (14.47 g, 50.4 mmol) in dioxane (30 mL) at 0° C. was added 4N HCl in dioxane (60 mL, 240 mmol). The reaction mixture was stirred at room temperature for 3.5 hours, diluted with 3 volumes of diethyl ether. The resulting dark brown precipitate was collected by filtration. It was then treated with saturated $NaHCO_3$ solution and was extracted with ethyl acetate. The solution was dried over $MgSO_4$, filtered and evaporated in vacuo to yield the title compound (4.88 g, 52%).

Example 1E 7-ethoxy-5,8-dihydronaphthalen-1-amine

The product of Example 1D (1.8 g, 9.63 mmol) and tert-butanol (2.13 g, 28.8 mmol) were dissolved in tetrahydrofuran (20 mL) in a 3-neck 1000 mL round-bottom flask, and the solution was cooled to −78° C. Ammonia (~35 mL) was condensed into the flask, then lithium metal was added (wire, 225 mg, 32.4 mmol) in portions over 10 min. The reaction mixture was stirred at −78° C. for 1 h, quenched with methanol (50 mL) and $H_2O$ (50 mL). The reaction was allowed to stir overnight at room temperature to allow $NH_3$ to evaporate, then it was diluted with ethyl acetate (300 mL), washed with $H_2O$ and brine, dried over $Na_2SO_4$, filtered and concentrated. The residue was purified on silica gel, eluting with 15%-25% ethyl acetate-hexanes, to afford the title compound as a brown oil (999 mg, 55%). $^1$H NMR (DMSO-$d_6$) δ 6.82 (t, 1H, J=7.6 Hz), 6.44 (d, 1H, J=7.1 Hz), 6.35 (d, 1H, J=7.5 Hz), 4.80 (s, 2H), 4.78 (t, 1H, J=3.8 Hz), 3.78 (q, 2H, J=7.1 Hz), 3.36 (q, 2H, 4.8 Hz), 3.00 (t, 2H, J=4.9 Hz), 1.26 (t, 3H, J=7.1 Hz); MS (DCI$^+$) m/z 190 (M+H).

Example 1F 2-ethoxy-8-isothiocyanato-1,4-dihydronaphthalene

A solution of the product of Example 1E (200 mg, 1.06 mmol) in dichloromethane (2.5 mL) was added to a solution of O,O-dipyridin-2-yl thiocarbonate (246 mg, 1.06 mmol) in dichloromethane (5 mL) at room temperature. After stirring at room temperature for 18 hours, the mixture was concentrated, then filtered through silica gel and eluted with 5% ethyl acetate-hexane. Evaporation of the filtrate in vacuo afforded the title compound as a pale pink solid, 225 mg (92%). $^1$H NMR (DMSO-$d_6$) δ 7.21-7.27 (m, 3H), 4.86 (t, 1H, J=3.6 Hz), 3.81 (q, 2H, J=7.0 Hz), 3.49 (q, 2H, 4.4 Hz), 3.35 (t, 2H, J=5.2 Hz), 1.27 (t, 3H, J=7.0 Hz); MS (DCI$^+$) m/z 232 (M+H).

Example 1G 2-azido-1-[4-(trifluoromethyl)phenyl]ethanone

The title compound was prepared using the procedure as described in Example 1B, substituting 2-bromo-1-[4-(trifluoromethyl)phenyl]ethanone for 2-bromo-1-(4-tert-butylphenyl)ethanone.

Example 1H

N-(7-ethoxy-5,8-dihydronaphthalen-1-yl)-5-[4-(trifluoromethyl)phenyl]-1,3-oxazol-2-amine A solution of the product of Example 1F (398 mg, 1.72 mmol), the product of Example 1G (473 mg, 2.07 mmol), and triphenyl phosphine (542 mg, 2.07 mmol) in dioxane (9 mL) was heated at 85° C. for 30 min. The solution was cooled to room temperature and evaporated in vacuo. The residue was chromatographed on silica gel, eluting with 25% ethyl acetate-hexane to afford the title compound as a yellow solid (150 mg, 22%). $^1$H NMR (DMSO-$d_6$) δ 9.38 (s, 1H), 7.76 (m, 4H), 7.65 (d, 1H, J=8.5 Hz), 7.62 (s, 1H), 7.18 (t, 1H, J=8.2 Hz), 6.97 (d, 1H, J=8.4 Hz), 4.85 (m, 1H), 3.79 (q, 2H, J=6.7 Hz), 3.49 (m, 2H), 3.36 (m, 2H), 1.26 (t, 3H, J=6.8 Hz); MS (ESI$^+$) m/z 401 (M+H)$^+$.

Example 1I 8-({5-[4-(trifluoromethyl)phenyl]-1,3-oxazol-2-yl}amino)-3,4-dihydronaphthalen-2(1H)-one A solution of the product of Example 1H (150 mg, 0.375 mmol) in tetrahydrofuran (2.3 mL) was treated with 2N HCl (0.76 mL, 1.52 mmol), and the mixture was heated at 40° C. for 1 hour. After cooling to room temperature, the solution was brought to pH 8 with saturated $NaHCO_3$ solution, and extracted with ethyl acetate. The organic extracts were washed with $H_2O$, dried over $Na_2SO_4$, filtered and evaporated in vacuo to the title compound as a brown residue (140 mg, 100%). $^1$H NMR (DMSO-$d_6$) δ 9.56 (s, 1H), 7.78 (m, 4H), 7.67 (d, 1H, J=7.8 Hz), 7.62 (s, 1H), 7.22 (t, 1H, J=7.8 Hz), 7.06 (d, 1H, J=7.4 Hz), 3.58 (s, 2H), 3.36 (m, 2H), 3.06 (t, 2H, J=6.8 Hz); MS (ESI$^+$) m/z 373 (M+H)$^+$.

Example 2

8-({5-[4-(trifluoromethyl)phenyl]-1,3-oxazol-2-yl}amino)-1,2,3,4-tetrahydronaphthalen-2-ol The product of Example 1I (60 mg, 0.161 mmol) in ethanol (6 mL) was treated at 0° C. with NaBH$_4$ (7 mg, 0.184 mmol). The reaction was stirred at 0° C. for 1 hour and was then poured into H$_2$O and extracted with ethyl acetate. The extracts were dried over Na$_2$SO$_4$, and concentrated in vacuo. The residue was chromatographed on silica gel eluting with 70%-85% ethyl acetate-hexane to afford the title compound as a tan solid (34 mg, 56%). $^1$H NMR (DMSO-d$_6$) δ 9.33 (s, 1H), 7.78 (m, 4H), 7.62 (s, 1H), 7.55 (d, 1H, J=7.4 Hz), 7.11 (m, 1H), 6.88 (d, 1H, J=7.2 Hz), 4.83 (d, 1H, J=4.1 Hz), 3.92 (m, 1H), 2.69-2.98 (m, 4H), 1.86 (m, 1H), 1.62 (m, 1H); MS (ESI$^+$) m/z 375 (M+H).

Example 3

8-{[5-(4-tert-butylphenyl)-1,3-oxazol-2-yl]amino}-1,2,3,4-tetrahydronaphthalen-2-ol Example 3A 5-(4-tert-butylphenyl)-N-(7-ethoxy-5,8-dihydronaphthalen-1-yl)-1,3-oxazol-2-amine The title compound was prepared using the procedure as described in Example 1H, substituting the product of Example 1B for the product of Example 1G.

Example 3B

8-{[5-(4-tert-butylphenyl)-1,3-oxazol-2-yl]amino}-3,4-dihydronaphthalen-2(1H)-one The title compound was prepared using the procedure of Example 1I, substituting the product of Example 3A for the product of Example 1H.

Example 3C

8-{[5-(4-tert-butylphenyl)-1,3-oxazol-2-yl]amino}-1,2,3,4-tetrahydronaphthalen-2-ol The title compound was prepared using the procedure of Example 2, substituting the product of Example 3B for the product of Example 1I. $^1$H NMR (DMSO-d$_6$) δ 9.07 (s, 1H), 7.58 (d, 1H, J=5.4 Hz), 7.46 (m, 3H), 7.30 (s, 1H), 7.08 (t, 1H, J=7.8 Hz), 6.83 (d, 1H, J=7.1 Hz), 4.80 (d, 1H, J=4.0 Hz), 3.91 (m, 1H), 2.72-2.96 (m, 4H), 1.86 (m, 1H), 1.62 (m, 1H), 1.29 (s, 9H); MS (ESI$^+$) m/z 363 (M+H).

Example 4

(2S)-8-{[5-(4-tert-butylphenyl)-1,3-oxazol-2-yl]amino}-1,2,3,4-tetrahydronaphthalen-2-ol The title compound was obtained by chromatographing the product of Example 3 using chiral HPLC (ChiralPak AD column, eluent: hexane-ethanol=75/25, flow rate=15 mL/min). $[\alpha]_D^{20}$=−48.0° (c 1.0, MeOH).

Example 5

(2R)-8-{[5-(4-tert-butylphenyl)-1,3-oxazol-2-yl]amino}-1,2,3,4-tetrahydronaphthalen-2-ol The title compound was obtained by chromatographing the product of Example 3 using chiral HPLC (ChiralPak AD column, eluent: hexane-ethanol=75/25, flow rate=15 mL/min). $[\alpha]_D^{20}$=+43.2° (c 1.0, MeOH).

Example 6

8-{[5-(4-chlorophenyl)-1,3-oxazol-2-yl]amino}-1,2,3,4-tetrahydronaphthalen-2-ol

Example 6A 2-azido-1-(4-chlorophenyl)ethanone

The title compound was prepared using the procedure as described in Example 1B, substituting 2-bromo-1-[4-chlorophenyl]ethan-1-one for the product of Example 1A.

Example 6B 5-(4-chlorophenyl)-N-(7-ethoxy-5,8-dihydronaphthalen-1-yl)-1,3-oxazol-2-amine The title compound was prepared using the procedure as described in Example 1H, substituting the product of Example 6A for the product of Example 1G.

Example 6C

8-{[5-(4-chlorophenyl)-1,3-oxazol-2-yl]amino}-3,4-dihydronaphthalen-2(1H)-one

The title compound was prepared using the procedure as described in Example 1I, substituting the product of Example 6B for the product of Example 1H.

Example 6D

8-{[5-(4-chlorophenyl)-1,3-oxazol-2-yl]amino}-1,2,3,4-tetrahydronaphthalen-2-ol

The title compound was prepared using the procedure as described in Example 2, substituting the product of Example 6C for the product of Example 1I. $^1$H NMR (DMSO-d$_6$) δ 9.16 (s, 1H), 7.43-7.57 (m, 6H), 7.09 (t, 1H, J=7.4 Hz), 6.83 (d, 1H, J=7.0 Hz), 4.80 (d, 1H, J=3.7 Hz), 3.92 (m, 1H), 2.72-2.98 (m, 4H), 1.86 (m, 1H), 1.61 (m, 1H); MS (ESI$^+$) m/z 341/343 (M+H, $^{35}$Cl/$^{37}$Cl).

Example 7

8-{[5-(4-pyrrolidin-1-ylphenyl)-1,3-oxazol-2-yl]amino}-1,2,3,4-tetrahydronaphthalen-2-ol Example 7A 2-azido-1-(4-pyrrolidin-1-ylphenyl)ethanone The title compound was prepared using the procedure as described in Example 1B, substituting 2-bromo-1-(4-pyrrolidin-1-ylphenyl)ethanone for the product of Example 1A.

Example 7B

N-(7-ethoxy-5,8-dihydronaphthalen-1-yl)-5-(4-pyrrolidin-1-ylphenyl)-1,3-oxazol-2-amine 5-(4-chlorophenyl)-N-(7-ethoxy-5,8-dihydronaphthalen-1-yl)-1,3-oxazol-2-amine The title compound was prepared using the procedure as described in Example 1H, substituting the product of Example 7A for the product of Example 1G.

Example 7C

8-{[5-(4-pyrrolidin-1-ylphenyl)-1,3-oxazol-2-yl]amino}-3,4-dihydronaphthalen-2(1H)-one The title compound was prepared using the procedure as described in Example 1I, substituting the product of Example 7B for the product of Example 1H.

Example 7D

8-{[5-(4-pyrrolidin-1-ylphenyl)-1,3-oxazol-2-yl]amino}-1,2,3,4-tetrahydronaphthalen-2-ol The title compound was prepared using the procedure as described in Example 2, substituting the product of Example 7C for the product of Example 1I. $^1$H NMR (DMSO-d$_6$) δ 8.86 (s, 1H), 7.61 (d, 2H, J=7.2 Hz), 7.37 (d, 1H, J=8.9 Hz), 7.07 (t, 1H, J=7.8 Hz), 7.02 (s, 1H), 6.80 (d, 1H, J=8.2 Hz), 6.57 (d, 2H, J=8.8 Hz), 4.79 (d, 1H, J=4.1 Hz), 3.91 (m, 1H), 3.25 (m, 4H), 2.66-2.97 (m, 4H), 1.99 (m, 4H), 1.89 (m, 1H), 1.62 (m, 1H); MS (ESI$^+$) m/z 376 (M+H).

Example 8

8-{[5-(4-bromophenyl)-1,3-oxazol-2-yl]amino}-1,2,3,4-tetrahydronaphthalen-2-ol

Example 8A 2-azido-1-(4-bromophenyl)ethanone

The title compound was prepared using the procedure as described in Example 1B, substituting 2-bromo-1-(4-bromophenyl)ethanone for the product of Example 1A.

Example 8B 5-(4-bromophenyl)-N-(7-ethoxy-5,8-dihydronaphthalen-1-yl)-1,3-oxazol-2-amine The title compound was prepared using the procedure as described in Example 1H, substituting the product of Example 8A for the product of Example 1G.

Example 8C

8-{[5-(4-bromophenyl)-1,3-oxazol-2-yl]amino}-3,4-dihydronaphthalen-2(1H)-one

The title compound was prepared using the procedure as described in Example 1I, substituting the product of Example 8B for the product of Example 1H.

Example 8D

8-{[5-(4-bromophenyl)-1,3-oxazol-2-yl]amino}-1,2,3,4-tetrahydronaphthalen-2-ol

The title compound was prepared using the procedure as described in Example 2, substituting the product of Example 8C for the product of Example 1I. $^1$H NMR (DMSO-d$_6$) δ 9.17 (s, 1H), 7.43-7.57 (m, 6H), 7.10 (t, 1H, J=7.3 Hz), 6.81 (d, 1H, J=6.8 Hz), 4.80 (d, 1H, J=3.9 Hz), 3.90 (m, 1H), 2.68-2.96 (m, 4H), 1.82 (m, 1H), 1.60 (m, 1H); MS (ESI$^+$) m/z 385/387 (M+H, $^{79}$Br/$^{81}$Br).

Example 9

8-{[5-(4-methylphenyl)-1,3-oxazol-2-yl]amino}-1,2,3,4-tetrahydronaphthalen-2-ol

Example 9A 2-azido-1-(4-methylphenyl)ethanone

The title compound was prepared using the procedure as described in Example 1B, substituting 2-bromo-1-(4-methylphenyl)ethanone for the product of Example 1A.

Example 9B

N-(7-ethoxy-5,8-dihydronaphthalen-1-yl)-5-(4-methylphenyl)-1,3-oxazol-2-amine

The title compound was prepared using the procedure as described in Example 1H, substituting the product of Example 9A for the product of Example 1G.

Example 9C

8-{[5-(4-methylphenyl)-1,3-oxazol-2-yl]amino}-3,4-dihydronaphthalen-2(1H)-one

The title compound was prepared using the procedure as described in Example 1I, substituting the product of Example 9B for the product of Example 1H.

Example 9D

8-{[5-(4-methylphenyl)-1,3-oxazol-2-yl]amino}-1,2,3,4-tetrahydronaphthalen-2-ol

The title compound was prepared using the procedure as described in Example 2, substituting the product of Example 9C for the product of Example 1I. $^1$H NMR (DMSO-d$_6$) δ 9.05 (s, 1H), 7.58 (m, 1H), 7.44 (m, 2H), 7.29 (s, 1H), 7.19 (m, 2H), 7.06 (t, 1H, J=7.5 Hz), 6.83 (d, 1H, J=7.0 Hz), 4.80 (d, 1H, J=4.0 Hz), 3.92 (m, 1H), 2.72-2.96 (m, 4H), 2.31 (s, 3H), 1.84 (m, 1H), 1.63 (m, 1H); MS (ESI$^+$) m/z 321 (M+H).

Example 10

8-{[5-(4-methoxyphenyl)-1,3-oxazol-2-yl]amino}-1,2,3,4-tetrahydronaphthalen-2-ol

Example 10A 2-azido-1-(4-methoxyphenyl)ethanone

The title compound was prepared using the procedure as described in Example 1B, substituting 2-bromo-1-(4-methoxyphenyl)ethanone for the product of Example 1A.

Example 10B

N-(7-ethoxy-5,8-dihydronaphthalen-1-yl)-5-(4-methoxyphenyl)-1,3-oxazol-2-amine

The title compound was prepared using the procedure as described in Example 1H, substituting the product of Example 10A for the product of Example 1G.

Example 10C

8-{[5-(4-methoxyphenyl)-1,3-oxazol-2-yl]amino}-3,4-dihydronaphthalen-2(1H)-one

The title compound was prepared using the procedure as described in Example 1I, substituting the product of Example 10B for the product of Example 1H.

Example 10D

8-{[5-(4-methoxyphenyl)-1,3-oxazol-2-yl]amino}-1,2,3,4-tetrahydronaphthalen-2-ol The title compound was prepared using the procedure as described in Example 2, substituting the product of Example 10C for the product of Example 1I. $^1$H NMR (DMSO-d$_6$) δ 8.98 (s, 1H), 7.59 (d, 1H, J=7.8 Hz), 7.49 (d, 2H, J=8.8 Hz), 7.20 (s, 1H), 7.08 (t, 1H, J=7.6 Hz), 7.00 (d, 2H, J=8.8 Hz), 6.82 (d, 1H, J=7.4 Hz), 4.79 (d, 1H, J=4.1 Hz), 3.93 (m, 1H), 3.78 (s, 3H), 2.74-2.98 (m, 4H), 1.85 (m, 1H), 1.63 (m, 1H); MS (ESI$^+$) m/z 337 (M+H).

Example 11

8-[(5-phenyl-1,3-oxazol-2-yl)amino]-1,2,3,4-tetrahydronaphthalen-2-ol

Example 11A 2-azido-1-phenylethanone

The title compound was prepared using the procedure as described in Example 1B, substituting 2-bromo-1-phenylethanone for the product of Example 1A.

Example 11B

N-(7-ethoxy-5,8-dihydronaphthalen-1-yl)-5-phenyl-1,3-oxazol-2-amine

The title compound was prepared using the procedure as described in Example 1H, substituting the product of Example 11A for the product of Example 1G.

Example 11C

8-[(5-phenyl-1,3-oxazol-2-yl)amino]-3,4-dihydronaphthalen-2(1H)-one

The title compound was prepared using the procedure as described in Example 1I, substituting the product of Example 11B for the product of Example 1H.

Example 11D

8-[(5-phenyl-1,3-oxazol-2-yl)amino]-1,2,3,4-tetrahydronaphthalen-2-ol

The title compound was prepared using the procedure as described in Example 2, substituting the product of Example 11C for the product of Example 1I. $^1$H NMR (DMSO-d$_6$) 9.11 (s, 1H), 7.59 (m, 3H), 7.41 (t, 2H, J=7.7 Hz), 7.37 (s, 1H), 7.25 (t, 1H, J=7.5 Hz), 7.09 (t, 1H, J=7.5 Hz), 6.84 (d, 1H, J=7.1 Hz), 4.80 (d, 1H, J=4.1 Hz), 3.93 (m, 1H), 2.73-2.99 (m, 4H), 1.86 (m, 1H), 1.62 (m, 1H); MS (ESI$^+$) m/z 307 (M+H).

Example 12

8-{[5-(1-adamantyl)-1,3-oxazol-2-yl]amino}-1,2,3,4-tetrahydronaphthalen-2-ol

Example 12A 1-(1-adamantyl)-2-azidoethanone

The title compound was prepared using the procedure as described in Example 1B, substituting 1-(1-adamantyl)-2-bromoethanone for the product of Example 1A.

Example 12B 5-(1-adamantyl)-N-(7-ethoxy-5,8-dihydronaphthalen-1-yl)-1,3-oxazol-2-amine The title compound was prepared using the procedure as described in Example 1H, substituting the product of Example 12A for the product of Example 1G.

Example 12C

8-{[5-(1-adamantyl)-1,3-oxazol-2-yl]amino}-3,4-dihydronaphthalen-2(1 h)-one

The title compound was prepared using the procedure as described in Example 1I, substituting the product of Example 12B for the product of Example 1H.

Example 12D

8-{[5-(1-adamantyl)-1,3-oxazol-2-yl]amino}-12,3,4-tetrahydronaphthalen-2-ol

The title compound was prepared using the procedure as described in Example 2, substituting the product of Example 12C for the product of Example 1I. $^1$H NMR (DMSO-d$_6$) δ 8.64 (s, 1H), 7.55 (d, 1H, J=7.7 Hz), 7.05 (t, 1H, J=7.6 Hz), 6.77 (d, 1H, J=7.1 Hz), 6.41 (s, 1H), 4.76 (d, 1H, J=4.1 Hz), 3.90 (m, 1H), 2.72-2.94 (m, 3H), 1.63-2.05 (m, 18H); MS (ESI$^+$) m/z 365 (M+H)$^+$.

Example 13

8-[(5-methyl-1,3-oxazol-2-yl)amino]-1,2,3,4-tetrahydronaphthalen-2-ol

Example 13A 1-azidoacetone

The title compound was prepared using the procedure as described in Example 1B, substituting 1-chloroacetone for the product of Example 1A.

Example 13B

N-(7-ethoxy-5,8-dihydronaphthalen-1-yl)-5-methyl-1,3-oxazol-2-amine

The title compound was prepared using the procedure as described in Example 1H, substituting the product of Example 13A for the product of Example 1G.

Example 13C

8-[(5-methyl-1,3-oxazol-2-yl)amino]-3,4-dihydronaphthalen-2(1H)-one

The title compound was prepared using the procedure as described in Example 1I, substituting the product of Example 13B for the product of Example 1H.

Example 13D

8-[(5-methyl-1,3-oxazol-2-yl)amino]-1,2,3,4-tetrahydronaphthalen-2-ol

The title compound was prepared using the procedure as described in Example 2, substituting the product of Example 13C for the product of Example 1I. $^1$H NMR (DMSO-d$_6$) m/z δ 8.64 (s, 1H), 7.55 (d, 1H, J=8.1 Hz), 7.03 (t, 1H, J=7.8 Hz), 6.76 (d, 1H, J=7.4 Hz), 6.48 (s, 1H), 4.77 (d, 1H, J=4.1 Hz), 3.90 (m, 1H), 2.63-2.93 (m, 4H), 2.20 (s, 3H), 1.83 (m, 1H), 1.60 (m, 1H); MS (ESI$^+$) m/z 245 (M+H)$^+$.

Example 14

8-{[5-(2-methylphenyl)-1,3-oxazol-2-yl]amino}-1,2,3,4-tetrahydronaphthalen-2-ol

Example 14A 2-azido-1-(2-methylphenyl)ethanone

The title compound was prepared using the procedure as described in Example 1B, substituting 2-bromo-1-(2-methylphenyl)ethanone for the product of Example 1A.

Example 14B

N-(7-ethoxy-5,8-dihydronaphthalen-1-yl)-5-(2-methylphenyl)-1,3-oxazol-2-amine

The title compound was prepared using the procedure as described in Example 1H, substituting the product of Example 14A for the product of Example 1G.

Example 14C

8-{[5-(2-methylphenyl)-1,3-oxazol-2-yl]amino}-3,4-dihydronaphthalen-2(1H)-one

The title compound was prepared using the procedure as described in Example 1I, substituting the product of Example 14B for the product of Example 1H.

Example 14D

8-{[5-(2-methylphenyl)-1,3-oxazol-2-yl]amino}-1,2,3,4-tetrahydronaphthalen-2-ol

The title compound was prepared using the procedure as described in Example 2, substituting the product of Example 14C for the product of Example 1I. $^1$H NMR (DMSO-d$_6$) δ 9.11 (s, 1H), 7.54-7.63 (m, 2H), 7.07-7.30 (m, 5H), 6.84 (d, 1H, J=7.1 Hz), 4.81 (d, 1H, J=4.1 Hz), 3.92 (m, 1H), 2.68-2.99 (m, 4H), 2.40 (s, 3H), 1.84 (m, 1H), 1.62 (m, 1H); MS (ESI$^+$) m/z 321 (M+H)$^+$.

Example 15

8-{[5-(3-methylphenyl)-1,3-oxazol-2-yl]amino}-1,2,3,4-tetrahydronaphthalen-2-ol

Example 15A 2-azido-1-(3-methylphenyl)ethanone

The title compound was prepared using the procedure as described in Example 1B, substituting 2-bromo-1-(3-methylphenyl)ethanone for the product of Example 1A.

Example 15B

N-(7-ethoxy-5,8-dihydronaphthalen-1-yl)-5-(3-methylphenyl)-1,3-oxazol-2-amine

The title compound was prepared using the procedure as described in Example 1H, substituting the product of Example 15A for the product of Example 1G.

Example 15C

8-{[5-(3-methylphenyl)-1,3-oxazol-2-yl]amino}-3,4-dihydronaphthalen-2(1H)-one

The title compound was prepared using the procedure as described in Example 1I, substituting the product of Example 15B for the product of Example 1H.

Example 15D

8-{[5-(3-methylphenyl)-1,3-oxazol-2-yl]amino}-1,2,3,4-tetrahydronaphthalen-2-ol

The title compound was prepared using the procedure as described in Example 2, substituting the product of Example 15C for the product of Example 1I. $^1$H NMR (DMSO-d$_6$) δ 9.08 (s, 1H), 7.58 (d, 1H, J=7.3 Hz), 7.26-7.39 (m, 4H), 7.04-7.12 (m, 2H), 6.83 (d, 1H, J=7.2 Hz), 4.81 (d, 1H, J=4.1

Hz), 3.93 (m, 1H), 2.73-2.97 (m, 4H), 2.33 (s, 3H), 1.86 (m, 1H), 1.61 (m, 1H); MS (ESI+) m/z 321 (M+H).

Example 16

8-[(5-benzyl-1,3-oxazol-2-yl)amino]-1,2,3,4-tetrahydronaphthalen-2-ol

Example 16A 1-bromo-3-phenylacetone

To a suspension of CuBr (0.143 g, 0.997 mmol) in 25 mL dry ether was slowly added 1M phenylmagnesium bromide (10 mL, 10 mmol). Epibromohydrin (0.87 mL, 10.5 mmol) was then added dropwise. The reaction mixture was allowed to stir at −78° C. to room temperature overnight, poured into $H_2O$ and extracted with ether. The extracts were washed with $H_2O$ and brine, dried over $Na_2SO_4$, filtered and evaporated in vacuo. The crude alcohol thus obtained was dissolved in acetone (400 mL) and chilled in ice, and to this solution was added dropwise 6 mL of Jones reagent (prepared by dissolution of 2.67 g $CrO_3$ in 2.5 mL $H_2SO_4$, followed by dilution with $H_2O$ to 10 mL). The reaction mixture was stirred at 0° C. for 15 min and was then evaporated in vacuo. The residue was taken up in ethyl acetate, washed repeatedly with water and once with brine, dried over $Na_2SO_4$, filtered and evaporated to afford the ketone product as a brown oil (1.6 g, 75%). $^1$H NMR (DMSO-$d_6$) δ 7.17-7.35 (m, 5H), 4.45 (s, 2H), 3.94 (s, 2H); MS (DCI+) m/z 230 (M+$NH_4^+$).

Example 16B 1-azido-3-phenylacetone

The title compound was prepared using the procedure as described in Example 1B, substituting the product of Example 16A for the product of Example 1A.

Example 16C 5-benzyl-N-(7-ethoxy-5,8-dihydronaphthalen-1-yl)-1,3-oxazol-2-amine

The title compound was prepared using the procedure as described in Example 1H, substituting the product of Example 16B for the product of Example 1G.

Example 16D

8-[(5-benzyl-1,3-oxazol-2-yl)amino]-3,4-dihydronaphthalen-2(1H)-one

The title compound was prepared using the procedure as described in Example 1I, substituting the product of Example 16C for the product of Example 1H.

Example 16E

8-[(5-benzyl-1,3-oxazol-2-yl)amino]-1,2,3,4-tetrahydronaphthalen-2-ol

The title compound was prepared using the procedure as described in Example 2, substituting the product of Example 16D for the product of Example 1I. $^1$H NMR (DMSO-$d_6$) δ 8.72 (s, 1H), 7.56-7.63 (m, 3H), 7.23-7.37 (m, 3H), 7.02 (t, 1H, J=7.5 Hz), 6.77 (d, 1H, J=7.3 Hz), 6.56 (s, 1H), 4.74 (d, 1H, J=3.7 Hz), 3.93 (s, 2H), 3.81 (m, 1H), 2.70-2.90 (m, 4H), 1.81 (m, 1H), 1.58 (m, 1H); MS (ESI+) m/z 321 (M+H)+.

Example 17

8-[(5-tert-butyl-1,3-oxazol-2-yl)amino]-1,23,4-tetrahydronaphthalen-2-ol

Example 17A 1-azido-3,3-dimethylbutan-2-one

A mixture of 1-bromopinacolone (0.5 mL, 3.7 mmol) and $NaN_3$ (0.48 g, 7.38 mmol) in 50 mL acetone was stirred overnight at room temperature. It was then poured into brine and extracted with dichloromethane. The extracts were washed with brine, were dried over $Na_2SO_4$, filtered, and were evaporated to afford the title compound as a yellow oil (524 mg, 100%). $^1$H NMR (DMSO-$d_6$) δ 4.39 (s, 2H), 1.10 (s, 9H); MS (DCI+) m/z 142 (M+H)+.

Example 17B 5-tert-butyl-N-(7-ethoxy-5,8-dihydronaphthalen-1-yl)-1,3-oxazol-2-amine The title compound was prepared using the procedure as described in Example 1H, substituting the product of Example 17A for the product of Example 1G.

Example 17C

8-[(5-tert-butyl-1,3-oxazol-2-yl)amino]-3,4-dihydronaphthalen-2(1H)-one

The title compound was prepared using the procedure as described in Example 1I, substituting the product of Example 17B for the product of Example 1H.

Example 17D

8-[(5-tert-butyl-1,3-oxazol-2-yl)amino]-1,2,3,4-tetrahydronaphthalen-2-ol

The title compound was prepared using the procedure as described in Example 2, substituting the product of Example 17C for the product of Example 1I. $^1$H NMR (DMSO-$d_6$) δ 8.66 (s, 1H), 7.53 (d, J=7.8 Hz, 1H), 7.01 (t, J=7.8 Hz, 1H), 6.75 (d, J=7.5 Hz, 1H), 6.44 (s, 1H), 4.76 (d, J=3.7 Hz, 1H), 3.94 (m, 1H), 2.61-2.99 (m, 4H), 1.84 (m, 1H), 1.60 (m, 1H), 1.22 (s, 9H); MS (ESI+) m/z 287 (M+H)+.

Example 18

8-(methyl{5-[4-(trifluoromethyl)phenyl]-1,3-oxazol-2-yl}amino)-1,2,3,4-tetrahydronaphthalen-2-ol Example 18A 8-amino-1,2,3,4-tetrahydronaphthalen-2-ol To the hydrogenation reaction vessel was charged 5 g of 8-amino-2-naphthanol, 0.2 g of 50% w/w NaOH, 100 ml ethanol, and 2 g of Raney Ni (wet 40 wt % load). The vessel was vacuum purged with hydrogen several times before heating to 85° C. and maintaining a hydrogen pressure of 1300 psi. The mixture was filtered after 6 hrs, and the filtrate concentrated to yield a brown solid. Isolated yield 4.97 g (97%). $^1$H NMR (500 MHz, DMSO-d$_6$) δ ppm 1.44-1.68 (m, 1H), 1.79-1.94 (m, 1H), 2.20 (dd, J=16.48, 7.63 Hz, 1H), 2.56-2.85 (m, 3H), 3.85-3.99 (m, 1H), 4.63 (s, 2H), 4.75 (d, J=4.12 Hz, 1H), 6.30 (d, J=7.48 Hz, 1H), 6.44 (d, J=7.78 Hz, 1H), 6.78 (t, J=7.63 Hz, 1H). $^{13}$C NMR (126 MHz, DMSO-d$_6$) δ ppm 27.35, 31.41, 33.36, 65.81, 111.35, 116.48, 119.13, 125.53, 136.00, 146.12.

Example 18B

7-{[tert-butyl(dimethyl)silyl]oxy}-5,6,7,8-tetrahydronaphthalen-1-amine

A mixture of the product of Example 18A (2.33 g, 14.3 mmol), tert-butylchlorodimethylsilane (2.6 g, 17.2 mmol), and imidazole (2.9 g, 42.3 mmol) was stirred in 40 mL of dichloromethane at rt overnight. The mixture was then washed several times with water and once with brine. Drying over Na$_2$SO$_4$, filtered and evaporation afforded the product as a dark purple oil, 2.6 g (65%). $^1$H NMR (DMSO-d$_6$) δ 6.77 (dd, J=7.8, 7.4 Hz, 1H), 6.42 (d, J=7.8 Hz, 1H), 6.28 (d, J=7.4 Hz, 1H), 4.7 (br s, 2H), 4.11 (m, 1H), 2.75 (m, 3H), 2.24 (m, 1H), 1.82 (m, 1H), 1.63 (m, 1H), 0.88 (s, 9H), 0.09 (s, 6H); MS (ESI$^+$) m/z 278 (M+H)$^+$.

Example 18C tert-butyl[(8-isothiocyanato-1,2,3,4-tetrahydronaphthalen-2-yl)oxy]dimethylsilane A solution of the product of Example 18B, 2-(tert-butyldimethylsilyl)-ol (1.4 g, 5.07 mmol) and di-2-pyridyl thionocarbonate (1.07 g, 4.61 mmol) in 30 mL dichloromethane was stirred at room temperature overnight. The mixture was evaporated, then the residue was taken up in 2 mL dichloromethane and filtered through silica gel, eluting with 5% ethyl acetate-hexane. Evaporation of the filtrate afforded the product as a dark red oil (1.165 g, 72%). $^1$H NMR (DMSO-d$_6$) δ 7.21 (m, 3H), 4.27 (m, 1H), 2.58-3.09 (m, 4H), 1.90 (m, 1H), 1.77 (m, 1H), 0.90 (s, 9H), 0.14 (s, 6H).

Example 18D

N-(7-{[tert-butyl(dimethyl)silyl]oxy}-5,6,7,8-tetrahydronaphthalen-1-yl)-5-[4-(trifluoromethyl)phenyl]-1,3-oxazol-2-amine The title compound was prepared using the procedure as described in Example 1H, substituting the product of Example 18C for the product of Example 1F.

Example 18E

N-(7-{[tert-butyl(dimethyl)silyl]oxy}-5,6,7,8-tetrahydronaphthalen-1-yl)-N-methyl-5-[4-(trifluoromethyl)phenyl]-1,3-oxazol-2-amine The product of Example 18D (300 mg, 0.615 mmol) in 5 mL N,N-dimethylformamide was treated with NaH (60% dispersion, 32 mg, 0.8 mmol) at rt. After stirring for 5 minutes, iodomethane (0.15 mL, 2.4 mmol) was added. The reaction was stirred at rt for 24 h, then it was poured into ethyl acetate and washed several times with water and once with brine. The organic layer was dried over Na$_2$SO$_4$ and was concentrated. The concentrate was purified on silica gel, eluting with 5% ethyl acetate-hexane and afforded the title compound as a brown oil (56 mg, 18%).

Example 18F 8-(methyl{5-[4-(trifluoromethyl)phenyl]-1,3-oxazol-2-yl}amino)-1,2,3,4-tetrahydronaphthalen-2-ol A solution of the product of Example 18E (56 mg, 0.112 mmol) in 6 mL of tetrahydrofuran was treated with a solution of tetrabutylammonium fluoride (1M-in-tetrahydrofuran, 1 mL, 1 mmol). The reaction mixture was stirred at rt for 4 h, then the solvent was evaporated, and the residue was chromatographed on silica gel, eluting with 70% ethyl acetate-hexane, to afford the title compound as a tan foam (27 mg, 62%). $^1$H NMR (DMSO-d$_6$) δ 7.70 (d, J=8.4 Hz, 2H), 7.58 (d, J=8.3 Hz, 2H), 7.57 (s, 1H), 7.11-7.22 (m, 3H), 4.78 (d, J=3.7 Hz, 1H), 3.86 (m, 1H), 3.38 (s, 3H), 2.73-2.98 (m, 3H), 2.37 (m, 1H), 1.89 (m, 1H), 1.63 (m, 1H); MS (ESI$^+$) m/z 389 (M+H)$^+$.

Example 19

N-[5-(4-tert-butylphenyl)-1,3-oxazol-2-yl]-N-(7-hydroxy-5,6,7,8-tetrahydronaphthalen-1-yl)acetamide The product of Example 3C (76 mg, 0.21 mmol) in 2 mL tetrahydrofuran was stirred with acetic anhydride (0.026 mL, 0.275 mmol) and triethylamine (0.088 mL, 0.63 mmol) at rt for 3 h. The reaction mixture was then diluted with ethyl acetate and washed with water and brine. The organic phase was dried over Na$_2$SO$_4$, filtered and concentrated. The residue was chromatographed on silica gel, eluting with 35% ethyl acetate-hexane and then 60% ethyl acetate-hexane to afford the title compound as a tan foam (38 mg, 45%). $^1$H NMR (DMSO-d$_6$) δ 8.03 (s, 1H), 7.48 (m, 4H), 7.10 (m, 2H), 6.82 (m, 1H), 4.72 (d, J=3.8 Hz, 1H), 3.92 (m, 1H), 2.84-3.02 (m, 3H), 2.73 (s, 3H), 2.44 (m, 1H), 1.86 (m, 1H), 1.61 (m, 1H), 1.27 (s, 9H); MS (ESI$^+$) m/z 405 (M+H)$^+$.

Example 20

N$^1$-(5-p-methylphenyloxazol-2-yl)-5,6,7,8-tetrahydronaphthalene-1,7-diamine

Example 20A (7-Hydroxy-5,6,7,8-tetrahydronaphthalen-1-yl)carbamic acid benzyl ester Benzylchloroformate (6.96 g, 40.8 mmol) was added dropwise to a solution of Example 18B (10.3 g, 37.1 mmol,) and diisopropylethylamine (7.20 g, 55.7 mmol) in 120 mL CH$_2$Cl$_2$ at 0° C. The mixture was stirred for 18 hours gradually warming to ambient temperature after which the volatiles were evaporated under reduced pressure. The residue was purified on silica gel eluting with 25% EtOAc/hexanes which yielded the benzyl carbamate as a light brown oil (15.2 g, 36.9 mmol). This product was taken up in 100 mL THF followed by addition of 1.79 g (111 mmol) of triethylamine trihydrofluoride. After 24 hours, the mixture was concentrated under reduced pressure and the residue partitioned between EtOAc and 1N aq. HCl. The separated organic layer was washed with 1N aq. HCl, brine, dried (Na$_2$SO$_4$), and concentrated under reduced pressure. The crude product was triturated with Et$_2$O, and the solid was collected by vacuum filtration and dried under vacuum at 50° C. resulting 8.82 g (80%) of the title compound as a white solid. $^1$H NMR (DMSO-d$_6$) δ 8.82 (s, 1H), 7.45-7.30 (m, 5H), 7.14 (d, J=7.0 Hz, 1H), 7.05 (t, J=7.0 Hz, 1H), 6.90 (d, J=7.0 Hz, 1H), 5.12 (s, 2H), 4.77 (d, J=3.7 Hz, 1H), 3.87 (m, 1H), 2.86 (m, 2H), 2.72 (m, 1H), 2.43 (m, 1H), 1.84 (m, 1H), 1.58 (m, 1H); MS (ESI$^+$) m/z 298 (M+H)$^+$.

Example 20B (7-Azido-5,6,7,8-tetrahydronaphthalen-1-yl)carbamic acid benzyl ester To a suspension of the product of Example 20A (5.05 g, 17.0 mmol) in 100 mL CH$_2$Cl$_2$ containing diisopropylethylamine (3.29 g, 25.5 mmol) at 0° C. was added methanesulfonyl chloride (2.15 g, 18.9 mmol) dropwise. After stirring 2 hours, the volatiles were evaporated under reduced pressure. The residue was partitioned between EtOAc and water, and the separated organic layer was washed with 1N aq. HCl, saturated NaHCO$_3$, brine, dried (Na$_2$SO$_4$), filtered and concentrated under reduced pressure. The crude product was dissolved in 60 mL DMF followed by addition of sodium azide. The mixture was heated to 75° C. for 1.5 hour then concentrated under reduced pressure. The residue was taken up in EtOAc and washed with water, brine, dried (Na$_2$SO$_4$), filtered and concentrated under reduced pressure. The crude product was triturated with 1:1 Et$_2$O:hexane and the solid collected by vacuum filtration and dried in air. The result was 4.68 g (85%) of the title compound as a pale orange solid. $^1$H NMR (DMSO-d$_6$) δ 8.95 (s, 1H), 7.45-7.30 (m, 5H), 7.19 (d, J=7 Hz, 1H), 7.10 (t, J=7 Hz, 1H), 6.94 (d, J=7 Hz, 1H), 5.13 (s, 2H), 4.00 (m, 1H), 2.96 (m, 1H), 2.83 (m, 2H), 2.62 (m, 1H), 1.99 (m, 1H), 1.74 (m, 1H); MS (ESI$^+$) m/z 323 (M+H)$^+$.

Example 20C (7-Amino-5,6,7,8-tetrahydronaphthalen-1-yl)carbamic acid benzyl ester Polymer supported triphenylphosphine (9.5 g, 28 mmol) was added to the product of Example 20B (4.6 g, 14 mmol) in THF (100 mL) containing 1.3 g (71 mmol) H$_2$O. The mixture was stirred for 48 hours at ambient temperature, then diluted with THF and filtered through a pad of celite. The filter cake was washed with 3 solvents systems sequentially comprising 100% CH$_3$OH, 1:1 CH$_3$OH:CH$_2$Cl$_2$, and 100% CH$_2$Cl$_2$. The filtrate was concentrated under reduced pressure to provide 3.5 g (83%) of the title compound. $^1$H NMR (DMSO-d$_6$) δ 8.81 (s, 1H), 7.45-7.30 (m, 5H), 7.13 (d, J=8 Hz, 1H), 7.05 (t, J=7 Hz, 1H), 6.90 (d, J=7 Hz, 1H), 5.12 (s, 2H), 3.00-2.65 (m, 4H), 2.23 (m, 1H), 1.84 (m, 1H), 1.59 (br s, 2H), 1.37 (m, 1H); MS (ESI$^+$) m/z 297 (M+H)$^+$.

Example 20D (8-Benzyloxycarbonylamino-1,2,34-tetrahydronaphthalen-2-yl)carbamic acid tert-butyl ester Di-t-butyldicarbonate (2.59 g, 11.9 mmol) was added to a solution of the product of Example 20C (3.52 g, 11.9 mmol) and diisopropylethylamine (2.30 g, 17.8 mmol) in 50 mL CH$_2$Cl$_2$ at ambient temperature. The mixture was stirred 18 hours and the volatiles were evaporated under reduced pressure. The residue was taken up in EtOAc and washed with 1N aq. HCl, saturated NaHCO$_3$, brine, dried (Na$_2$SO$_4$), filtered and concentrated under reduced pressure. Flash chromatography (30% EtOAc/hexanes) yielded 3.73 g (79%) of the title compound as a white solid. $^1$H NMR (DMSO-d$_6$) δ 8.87 (br s, 1H), 7.45-7.30 (m, 5H), 7.10 (m, 2H), 6.93 (m, 2H), 5.12 (s, 2H), 3.80 (m, 1H), 2.90 (m, 1H), 2.81 (m, 2H), 2.38 (m, 1H), 1.87 (m, 1H), 1.55 (m, 1H), 1.40 (s, 9H); MS (ESI$^+$) m/z 419 (M+Na)$^+$.

Example 20E (8-Amino-1,2,3,4-tetrahydronaphthalen-2-yl)carbamic acid tert-butyl ester To a solution of the product of Example 20D (3.73 g, 9.41 mmol) in 80 mL methanol was added 0.75 g 20% Pd(OH)$_2$/C. The mixture was shaken under 60 psi H$_2$ for 4 hours. The catalyst was then filtered and the filtrate concentrated under reduced pressure. The crude product was purified by flash chromatography eluting with 2% to 5% CH$_3$OH/CH$_2$Cl$_2$ which gave 2.33 g (94%) of the title compound as a white solid. $^1$H NMR (DMSO-d$_6$) δ 6.91 (br d, 1H), 6.77 (t, J=7.6 Hz, 1H), 6.42 (d, J=7.1 Hz, 1H), 6.29 (d, J=7.1 Hz, 1H), 4.69 (br s, 2H), 3.63 (m, 1H), 2.68 (m, 3H), 2.12 (m, 1H), 1.83 (m, 1H), 1.52 (m, 1H), 1.40 (s, 9H); MS (ESI$^+$) m/z 263 (M+H)$^+$.

Example 20F (8-Isothiocyanato-1,2,3,4-tetrahydronaphthalen-2-yl) carbamic acid tert-butyl ester The title compound was prepared using the procedure as described in Example 1F, substituting the product of Example 20E (1.02 g, 3.89 mmol) for 7-ethoxy-5,8-dihydronaphthalen-1-amine. $^1$H NMR (DMSO-d$_6$) δ 7.25-7.10 (m, 3H), 7.00 (m, 1H), 3.70 (m, 1H), 2.98 (m, 1H), 2.81 (m, 2H), 2.57 (m, 1H), 1.90 (m, 1H), 1.58 (m, 1H), 1.41 (s, 9H); MS (ESI$^+$) m/z 305 (M+H)$^+$.

Example 20G

[8-(5-p-methylphenyloxazol-2-ylamino)-1,2,3,4-tetrahydronaphthalen-2-yl]carbamic acid tert-butyl ester The title compound was prepared using the procedure as described in Example 1H, substituting the product of Example 20F (188 mg, 0.618 mmol) for the product of Example 1F and the product of Example 9A (130 mg, 0.741 mmol) for the product of Example 1G. The crude product was purified by flash chromatography eluting with 2% to 5% CH$_3$OH/CH$_2$Cl$_2$ followed by 60% EtOAc/hexanes which gave 215 mg (83%) of the title compound as a yellow amorphous solid. $^1$H NMR (DMSO-d$_6$) δ 9.06 (br s, 1H), 7.60 (d, J=7.8 Hz, 1H), 7.45 (d, J=8.1 Hz, 2H), 7.29 (s, 1H), 7.23 (d, J=8.1 Hz, 2H), 7.10 (t, J=7.8 Hz, 1H), 6.98 (br d, 1H), 6.84 (d, J=7.5 Hz, 1H), 3.65 (m, 1H), 3.02 (m, 1H), 2.83 (m, 2H), 2.42 (m, 1H), 2.31 (s, 3H), 1.87 (m, 1H), 1.58 (m, 1H), 1.39 (s, 9H); MS (ESI$^+$) m/z 420 (M+H)$^+$.

Example 20H

N$^1$-(5-p-methylphenyloxazol-2-yl)-5,6,7,8-tetrahydronaphthalene-1,7-diamine

Hydrogen chloride in dioxane (4N, 7 mL, 28 mmol) was added to a suspension of 199 mg (0.474 mmol) of the product of Example 20G in 1 mL dioxane. After stirring 45 minutes, the mixture was quenched with 3N NaOH solution, then diluted with EtOAc and poured into water. The separated organic phase was washed with brine, dried (Na$_2$SO$_4$), filtered and concentrated under reduced pressure. The crude product was triturated with Et$_2$O and the solid was collected by vacuum filtration. The result was 92 mg (61%) of the title compound as a pale pink solid. $^1$H NMR (DMSO-d$_6$) δ 9.02 (br s, 1H), 7.57 (d, J=7.1 Hz, 1H), 7.45 (d, J=8.1 Hz, 2H), 7.28 (s, 1H), 7.23 (d, J=8.1 Hz, 2H), 7.08 (t, J=7.8 Hz, 1H), 6.83 (d, J=7.1 Hz, 1H), 3.05-2.70 (m, 4H), 2.31 (m, 4H), 1.85 (m, 3H), 1.42 (m, 1H); MS (ESI$^+$) m/z 320 (M+H)$^+$.

Example 21

N$^1$-[5-(4-Trifluoromethylphenyl)oxazol-2-yl]-5,6,7,8-tetrahydronaphthalene-1,7-diamine Example 21A {8-[5-(4-Trifluoromethylphenyl)oxazol-2-ylamino]-1,2,3,4-tetrahydro-naphthalen-2-yl}carbamic acid tert-butyl ester The title compound was prepared using the procedure as described in Example 1H, substituting the product of Example 20F (215 mg, 0.706 mmol) for the product of Example 1F, and the product of Example 1G (194 mg, 0.848 mmol). The crude product was purified by flash chromatography eluting with 20% EtOAc/hexane which gave 123 mg (37%) of the title compound as a white solid. $^1$H NMR (DMSO-d$_6$) δ 9.32 (br s, 1H), 7.75 (m, 4H), 7.60 (s, 1H), 7.55 (d, J=7.8 Hz, 1H), 7.12 (t, J=7.8 Hz, 1H), 6.98 (br d, 1H), 6.88 (d, J=7.5 Hz, 1H), 3.64 (m, 1H), 3.02 (m, 1H), 2.84 (m, 2H), 2.42 (m, 1H), 1.87 (m, 1H), 1.60 (m, 1H), 1.39 (s, 9H); MS (ESI$^+$) m/z 474 (M+H)$^+$.

Example 21B

N$^1$-[5-(4-Trifluoromethylphenyl)oxazol-2-yl]-5,6,7,8-tetrahydronaphthalene-1,7-diamine The title compound was prepared using the procedure as described in Example 20H substituting the product of Example 21A (120 mg, 0.253 mmol) for the product of Example 20G. The crude product was purified by trituration with Et$_2$O/hexanes which resulted in 36 mg (38%) of the title compound as a white solid. $^1$H NMR (DMSO-d$_6$) δ 9.32 (br s, 1H), 7.75 (m, 4H), 7.60 (s, 1H), 7.55 (d, J=7.8 Hz, 1H), 7.10 (t, J=7.8 Hz, 1H), 6.87 (d, J=7.8 Hz, 1H), 3.05-2.70 (m, 4H), 2.30 (m, 1H), 1.82 (m, 3H), 1.43 (m, 1H); MS (ESI$^+$) m/z 374 (M+H)$^+$.

Example 22

N$^1$-[5-(2-Fluoro-4-trifluoromethylphenyl)oxazol-2-yl]-5,6,7,8-tetrahydronaphthalene-1,7-diamine Example 22A 2-Azido-1-(2-fluoro-4-trifluoromethylphenyl)ethanone The title compound was prepared using the procedure as described in Example 1B, substituting 2-Bromo-1-(2-fluoro-4-trifluoromethylphenyl)ethanone for 2-bromo-1-(4-tert-butylphenyl)ethanone.

Example 22B

{8-[5-(2-Fluoro-4-trifluoromethylphenyl)oxazol-2-ylamino]-1,2,3,4-tetrahydronaphthalen-2-yl}carbamic acid tert-butyl ester The title compound was prepared using the procedure as described in Example 1H, substituting the product of Example 20F (415 mg, 1.36 mmol) for the product of Example 1F and the product of Example 22A (404 mg, 1.63 mmol) for the product of Example 1G. The crude product was purified by flash chromatography eluting with 20% to 60% EtOAc/hexanes which gave 107 mg (16%) of the title compound as a yellow solid.

Example 22C

N$^1$-[5-(2-Fluoro-4-trifluoromethylphenyl)oxazol-2-yl]-5,6,7,8-tetrahydronaphthalene-1,7-diamine Iodotrimethylsilane (52 mg, 0.260 mmol) was added dropwise to a solution of the product of Example 22B (107 mg, 0.218 mmol) in 1 mL CH$_2$Cl$_2$ at ambient temperature. After 15 minutes the reaction was diluted with CH$_2$Cl$_2$ and quenched with 1N aq NaOH solution. The mixture was stirred 15 minutes and then poured into water. The separated organic layer was washed with brine, dried (Na$_2$SO$_4$), filtered and concentrated in vacuo. The crude product was triturated with Et$_2$O/hexanes and the solid collected by vacuum filtration and dried under high vacuum. The result was 36 mg (42%) of the title compound as a white solid. $^1$H NMR (DMSO-d$_6$) δ 9.42 (br s, 1H), 7.75 (m, 3H), 7.52 (d, J=8.1 Hz, 1H), 7.44 (d, J=3.7 Hz, 1H), 7.11 (t, J=7.5 Hz, 1H), 6.88 (d, J=7.5 Hz, 1H), 3.05-2.70 (m, 4H), 2.30 (m, 1H), 1.86 (m, 1H), 1.70 (br s, 2H), 1.43 (m, 1H); MS (ESI$^+$) m/z 392 (M+H)$^+$.

Example 23

N-[8-(5-p-methylphenyloxazol-2-ylamino)-1,2,3,4-tetrahydronaphthalen-2-yl]methanesulfonamide Example 23A (7-Methanesulfonylamino-5,6,7,8-tetrahydronaphthalen-1-yl)carbamic acid benzyl ester Methanesulfonyl chloride (176 mg, 1.54 mmol) was added dropwise to a solution of the product from Example 20C (381 mg, 1.29 mmol) and diisopropylethylamine (332 mg, 2.57 mmol) in 15 mL CH$_2$Cl$_2$ at ambient temperature. The mixture was stirred 30 minutes, diluted with methylene chloride and poured into water. The separated organic phase was washed with 1N aq HCl, brine, dried (Na$_2$SO$_4$), filtered and concentrated under reduced pressure. Flash chromatography (4% CH$_3$OH/CH$_2$Cl$_2$) yielded 281 mg (58%) of the title compound as a white amorphous solid. $^1$H NMR (DMSO-d$_6$) δ 8.92 (s, 1H), 7.45-7.30 (m, 5H), 7.22 (d, J=7.1 Hz, 1H), 7.15 (m, 1H), 7.08 (t, J=7.5 Hz, 1H), 6.93 (m, 1H), 5.13 (s, 2H), 3.51 (m, 1H), 3.02 (m, 1H), 2.96 (s, 3H), 2.85 (m, 2H), 2.50 (m, 1H+DMSO), 2.01 (m, 1H), 1.61 (m, 1H); MS (ESI$^+$) m/z 375 (M+H)$^+$.

Example 23B

N-(8-Amino-1,2,3,4-tetrahydronaphthalen-2-yl)methanesulfonamide

The title compound was prepared using the procedure as described in Example 20E substituting the product of Example 23A (280 mg, 0.748 mmol) for the product Example 20D. Flash chromatography (5% to 10% CH$_3$OH/CH$_2$Cl$_2$)

gave 129 mg (72%) of the title compound as a white solid. $^1$H NMR (DMSO-d$_6$) δ 7.20 (d, J=7.5 Hz, 1H), 6.79 (t, J=7.8 Hz, 1H), 6.43 (m, 1H), 6.30 (m, 1H), 4.74 (s, 2H), 3.55 (m, 1H), 2.99 (s, 3H), 2.75 (m, 3H), 2.22 (m, 1H), 1.95 (m, 1H), 1.58 (m, 1H); MS (DCI$^+$) m/z 241 (M+H)$^+$.

Example 23C

N-(8-Isothiocyanato-1,2,3,4-tetrahydronaphthalen-2-yl)methanesulfonamide

The title compound was prepared using the procedure as described in Example 1F, substituting the product of Example 23B (125 mg, 0.529 mmol) for 7-ethoxy-5,8-dihydronaphthalen-1-amine. Flash chromatography eluting with 3% to 6% CH$_3$OH/CH$_2$Cl$_2$ gave 131 mg (89%) of the title compound as a white solid. $^1$H NMR (DMSO-d$_6$) δ 7.24 (m, 2H), 7.19 (d, J=7.8 Hz, 1H), 7.14 (m, 1H), 3.66 (m, 1H), 3.09 (m, 1H), 3.00 (s, 3H), 2.85 (m, 2H), 2.66 (m, 1H), 2.01 (m, 1H), 1.69 (m, 1H); MS (DCI$^+$) m/z 300 (M+NH$_4$)$^+$.

Example 23D

N-[8-(5-p-methylphenyloxazol-2-ylamino)-1,2,3,4-tetrahydronaphthalen-2-yl]methanesulfonamide The title compound was prepared using the procedure as described in Example 1H, substituting the product of Example 23C (128 mg, 0.453 mmol) for the product of Example 1F and the product of Example 9A (95 mg, 0.544 mmol) for the product of Example 1G. The crude product was purified by flash chromatography eluting with 2% to 5% CH$_3$OH/CH$_2$Cl$_2$ followed by 100% EtOAc which gave 116 mg (64%) of the title compound as a tan solid. $^1$H NMR (DMSO-d$_6$) δ 9.13 (s, 1H), 7.61 (d, J=7.5 Hz, 1H), 7.46 (d, J=8.1 Hz, 2H), 7.30 (s, 1H), 7.23 (m, 3H), 7.11 (t, J=7.8 Hz, 1H), 6.85 (d, J=7.5 Hz, 1H), 3.58 (m, 1H), 3.11 (m, 1H), 2.99 (s, 3H), 2.87 (m, 2H), 2.56 (m, 1H), 2.31 (s, 3H), 2.01 (m, 1H), 1.66 (m, 1H); MS (ESI$^+$) m/z 398 (M+H)$^+$.

Example 24

8-(5-Phenylthiazol-2-ylamino)-1,2,3,4-tetrahydronaphthalen-2-ol

Example 24A

[7-(tert-Butyldimethylsilyloxy)-5,6,7,8-tetrahydronaphthalen-1-yl]thiourea

A solution of the product of Example 18C (1.25 g, 3.91 mmol) in THF (50 mL) was treated with 7N methanolic NH$_3$ (5.6 mL, 39.1 mmol), and the mixture was stirred at room temperature for 6 hours. The mixture was partitioned between EtOAc and H$_2$O, and the separated organic phase was washed with brine, dried over Na$_2$SO$_4$, filtered and evaporated under reduced pressure. Silica gel chromatography (98:2 to 95:5 CH$_2$Cl$_2$:CH$_3$OH eluant) provided the title compound as a pale yellow solid, 1.27 g (97%). $^1$H NMR (300 MHz, DMSO-d$_6$) δ 9.12 (s, 1H), 6.6-7.8 (br, 2H), 6.99-7.13 (m, 3H), 4.08 (m, 1H), 2.73-2.92 (m, 4H), 1.84-1.92 (m, 1H), 1.60-1.68 (m, 1H). MS (ESI$^+$) m/z 337 (M+H).

Example 24B (1-Bromo-2,2-dimethoxyethyl)benzene (1-Bromo-2,2-dimethoxyethyl)benzene was synthesized according to the procedure of Rasmussen and Bowadt (*Synthesis* 1989, 114). A solution of phenylacetaldehyde (60 g, 500 mmol) in 250 mL MeOH was treated with 12.5 g of activated 3Å molecular sieves and was then brought to reflux with mechanical stirring. Bromine (25.6 mL, 500 mmol) was added dropwise. The mixture was refluxed for 5 hours, cooled to ambient temperature, and then treated with potassium carbonate (35.4 g, 257 mmol). Stirring was continued for 1 hour after which the solids were filtered off. The filtrate was treated with brine (250 mL), and extracted with pentane (150 mL). Evaporation of the solvent afforded the title compound as a brown oil, 77.71 g (63%), which was used without further purification.

Example 24C 8-(5-Phenylthiazol-2-ylamino)-1,2,3,4-tetrahydronaphthalen-2-ol

A mixture of the product of Example 24A (200 mg, 0.594 mmol) and the product of Example 24B (146 mg, 0.596 mmol) was refluxed for 2 hours in a mixture of EtOH (6 mL) and 1N HCl (1 mL). After cooling to room temperature, the mixture was quenched with saturated NaHCO$_3$ solution and was extracted with EtOAc. The extracts were dried over Na$_2$SO$_4$, filtered evaporated under reduced pressure, and chromatographed on silica gel (95:5 to 92:8 CH$_2$Cl$_2$:CH$_3$OH eluant). The title compound was afforded as a pale tan solid, 53 mg (28%). $^1$H NMR (DMSO-d$_6$) δ 9.29 (s, 1H), 7.57 (m, 2H), 7.46-7.49 (m, 2H), 7.33-7.38 (m, 2H), 7.22 (m, 1H), 7.10 (m, 1H), 6.88 (d, J=7.4 Hz, 1H), 4.82 (d, J=4.0 Hz, 1H), 3.82 (m, 1H), 2.71-2.98 (m, 4H), 1.83-1.93 (m, 1H), 1.57-1.66 (m, 1H). MS (ESI$^+$) m/z 323 (M+H). Anal. calcd. For C$_{19}$H$_{18}$N$_2$OS: C, 70.78; H, 5.63; N, 8.69. Found: C, 70.91; H, 5.37; N, 8.33.

Biological Activity

In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS)(with 1 mg/mL glucose and 3.6 mg/l Na pyruvate)(without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+ RNA supplied by Clontech (Palo Alto, Calif.) using primers designed surrounding the initiation and termination codons identical to the published sequences (Hayes et al. Pain 88: 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 μg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 μg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 μM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 μL per well of fluo-4 AM (2 μM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 μL of the compound solutions were added to the cells at the 10 second time mark of the experimental run. Then, after a 3 minute time delay, 50 μL of the capsaicin solution was added at the 190 second time mark (0.05 μM final concentration) (final volume=200 μL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 μM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ lower than 12 μM, preferably lower than 5 μM, more preferably less than 1 μM, and most preferably less than 0.1 μM.

In Vivo Data—Determination of Antinociceptive Effect

Experiments were performed on 400 adult male 129J mice (Jackson Laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee. The Complete Freund's Adjuvant-induced Thermal Hyperalgesia (CFA) assay described in Pircio et al. *Eur J Pharmacol.* Vol. 31(2) pages 207-215 (1975). Chronic inflammatory hyperalgesia was induced in one group of rats following the injection of complete Freund's adjuvant (CFA, 50%, 150 μL) into the plantar surface of the right hindpaw 48 hours prior to testing. Thermal nociceptive thresholds were measured in three different groups of rats. The $ED_{50s}$ were determined based on the oral administration.

The in vitro and in vivo data demonstrates that compounds of the present invention antagonize the VR1 receptor and are useful for treating pain, bladder overactivity, and urinary incontinence.

What is claimed is:
1. A compound of formula (I)

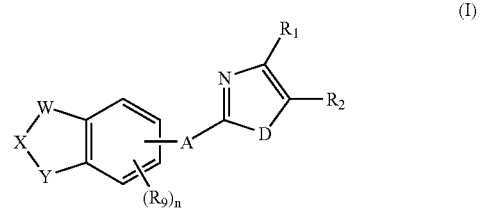

or a pharmaceutically acceptable salt, amide or ester thereof, wherein

A is —$N(R_3)$;

D is O or S;

$R_3$ and $R_4$ are each independently selected from the group consisting of hydrogen, alkyl, —C(O)alkyl, and —$S(O)_2$(alkyl);

$R_1$ and $R_2$ are each independently selected from the group consisting of hydrogen, alkyl, alkenyl, cyano, nitro, halogen, —$OR_5$, —$OC(O)R_5$, —$SR_5$, —$S(O)_2R_5$, —$S(O)_2OR_5$, —$S(O)_2N(R_5)(R_6)$, —$N(R_5)(R_6)$, —$N(R_6)C(O)R_5$, —$N(R_6)C(O)N(R_5)(R_6)$, —$N(R_6)S(O)_2N(R_5)(R_6)$, —$C(O)R_5$, —$C(O)OR_5$, haloalkyl, -alkylenyl-$OR_5$, -alkylenyl-$OC(O)R_5$, -alkylenyl-$SR_5$, -alkylenyl-$S(O)_2R_5$, -alkylenyl-$S(O)_2OR_5$, -alkylenyl-$S(O)_2N(R_5)(R_6)$, -alkylenyl-$N(R_5)(R_6)$, -alkylenyl-$N(R_6)C(O)R_5$, -alkylenyl-$N(R_6)C(O)N(R_5)(R_6)$, -alkylenyl-$N(R_6)S(O)_2N(R_5)(R_6)$, -alkylenyl-$C(O)R_5$, -alkylenyl-$C(O)OR_5$, -alkylenyl-$C(O)N(R_5)(R_6)$, —$R_7$, and -alkylenyl-$R_7$; provided that when one of $R_1$ and $R_2$ is hydrogen, the other is not hydrogen;

$R_5$ at each occurrence is independently selected from the group consisting of hydrogen, alkyl, alkenyl, haloalkyl and benzyl;

$R_6$ at each occurrence is independently selected from the group consisting of hydrogen and alkyl;

$R_7$ at each occurrence is independently selected from the group consisting of cycloalkyl, cycloalkenyl, heterocycle, aryl and heteroaryl; wherein each $R_7$ is independently substituted with 0, 1, 2, 3, 4 or 5 substituents independently selected from the group consisting of alkyl, alkenyl, halogen, cyano, nitro, hydroxy, alkoxy, haloalkoxy, —S(alkyl), —$S(O)_2$(alkyl), —$N(H)_2$, —N(H)(alkyl), —$N(alkyl)_2$, —N(H)C(O)alkyl, —C(O)OH, —C(O)Oalkyl, —$C(O)NH_2$, —C(O)N(H)alkyl, —$C(O)N(alkyl)_2$, —$R_8$, cyanoalkyl, haloalkyl, hydroxyalkyl, alkoxyalkyl, haloalkoxyalkyl, -alkylenyl-S(alkyl), -alkylenyl-$S(O)_2$(alkyl), -alkylenyl-$N(H)_2$, -alkylenyl-N(H)(alkyl), -alkylenyl-$N(alkyl)_2$, -alkylenyl-N(H)C(O)alkyl, -alkylenyl-C(O)OH, -alkylenyl-C(O)Oalkyl, -alkylenyl-$C(O)NH_2$, -alkylenyl-C(O)N(H)alkyl, -alkylenyl-$C(O)N(alkyl)_2$, and -alkylenyl-$R_8$;

$R_8$ at each occurrence is independently selected from the group consisting of cycloalkyl, cycloalkenyl, heterocycle, aryl and heteroaryl; wherein each $R_8$ is independently substituted with 0, 1, 2, 3, 4 or 5 substituents independently selected from the group consisting of alkyl, alkenyl, halogen, cyano, nitro, hydroxy, alkoxy, haloalkoxy, —S(alkyl), —S(O)$_2$(alkyl), —N(H)$_2$, —N(H)(alkyl), —N(alkyl)$_2$, —N(H)C(O)alkyl, —C(O)OH, —C(O)Oalkyl, —C(O)NH$_2$, —C(O)N(H)alkyl, —C(O)N(alkyl)$_2$, cyanoalkyl, haloalkyl, hydroxyalkyl, alkoxyalkyl, haloalkoxyalkyl, -alkylenyl-S(alkyl), -alkylenyl-S(O)$_2$(alkyl), -alkylenyl-N(H)$_2$, -alkylenyl-N(H)(alkyl), -alkylenyl-N(alkyl)$_2$, -alkylenyl-N(H)C(O)alkyl, -alkylenyl-C(O)OH, -alkylenyl-C(O)Oalkyl, -alkylenyl-C(O)NH$_2$, -alkylenyl-C(O)N(H)alkyl, and -alkylenyl-C(O)N(alkyl)$_2$;

W and Y are each independently selected from the group consisting of —C(R$_x$)(R$_y$)— and —N(R$_z$)—; provided that when one of W and Y is —N(R$_z$)—, then the other is —C(R$_x$)(R$_y$)—;

X is —C(R$_x$)(R$_y$)—C(R$_x$)(R$_y$)—,

R$_x$ and R$_y$ at each occurrence are each independently selected from the group consisting of hydrogen, alkyl, haloalkyl, —OR$_a$, —OC(O)R$_a$, —SR$_a$, —S(O)$_2$R$_a$, —S(O)$_2$N(R$_a$)(R$_b$), —S(O)$_2$OR$_a$, —N(R$_a$)(R$_b$), —N(R$_b$)C(O)R$_a$, —N(R$_b$)C(O)N(R$_a$)(R$_b$), —N(R$_b$)S(O)$_2$N(R$_a$)(R$_b$), —C(O)OR$_a$, —C(O)R$_a$, —C(O)N(R$_a$)(R$_b$), -alkylenyl-OR$_a$, -alkylenyl-OC(O)R$_a$, -alkylenyl-SR$_a$, -alkylenyl-S(O)$_2$R$_a$, -alkylenyl-S(O)$_2$N(R$_a$)(R$_b$), -alkylenyl-S(O)$_2$OR$_a$, -alkylenyl-N(R$_a$)(R$_b$), -alkylenyl-N(R$_b$)C(O)R$_a$, -alkylenyl-N(R$_b$)C(O)N(R$_a$)(R$_b$), -alkylenyl-N(R$_b$)S(O)$_2$N(R$_a$)(R$_b$), -alkylenyl-C(O)OR$_a$, -alkylenyl-C(O)R$_a$, -alkylenyl-C(O)N(R$_a$)(R$_b$), —R$_8$ and -alkylenyl-R$_8$;

R$_a$ at each occurrence is independently selected from the group consisting of hydrogen, alkyl, haloalkyl, —R$_8$ and -alkylenyl-R$_8$;

R$_b$ at each occurrence is independently selected from the group consisting of hydrogen, alkyl and haloalkyl; alternatively, R$_a$ and R$_b$ together with the nitrogen atom to which they are attached form a heterocycle ring substituted with 0, 1, 2, 3, 4 or 5 substituents independently selected from the group consisting of halogen, alkyl and haloalkyl;

R$_z$ at each occurrence is independently selected from the group consisting of hydrogen, alkyl, —C(O)alkyl, and —S(O)$_2$(alkyl);

R$_9$ at each occurrence is independently selected from the group consisting of halogen, alkyl, haloalkyl, hydroxyalkyl, alkoxyalkyl and haloalkoxyalkyl; and n is 0, 1, 2, or 3.

2. The compound of formula (I) according to claim 1, wherein D is —N(R$_4$).

3. The compound according to claim 2, wherein A is O.

4. The compound according to claim 2, wherein A is —N(R$_3$).

5. The compound of formula (I) according to claim 1, wherein D is S.

6. The compound according to claim 5, wherein A is O.

7. The compound according to claim 5, wherein A is —N(R$_3$).

8. The compound of formula (I) according to claim 1, wherein D is O.

9. The compound of formula (I) according to claim 8, wherein A is O.

10. The compound according to claim 8, wherein A is —N(R$_3$).

11. The compound according to claim 10, wherein R$_3$ is hydrogen.

12. The compound according to claim 11, wherein R$_2$ is —R$_7$ and R$_1$ is hydrogen.

13. The compound according to claim 12, wherein —R$_7$ is aryl.

14. The compound according to claim 13, wherein —R$_7$ is phenyl.

15. The compound according to claim 14, wherein
W is —C(R$_x$)(R$_y$);
Y is —C(R$_x$)(R$_y$); and
X is —C(O)—C(R$_x$)(R$_y$)—.

16. The compound according to claim 15, wherein R$_x$ and R$_y$ are hydrogen.

17. The compound according to claim 16, wherein the compound is selected from the group consisting of:
8-({5-[4-(trifluoromethyl)phenyl]-1,3-oxazol-2-yl}amino)-3,4-dihydronaphthalen-2(1H)—one;
8-{[5-(4-tert-butylphenyl)-1,3-oxazol-2-yl]amino}-3,4-dihydronaphthalen-2(1H)-one;
8-{[5-(4-chlorophenyl)-1,3-oxazol-2-yl]amino}-3,4-dihydronaphthalen-2(1H)-one;
8-{[5-(4-bromophenyl)-1,3-oxazol-2-yl]amino}-3,4-dihydronaphthalen-2(1H)-one;
8-{[5-(4-methoxyphenyl)-1,3-oxazol-2-yl]amino}-3,4-dihydronaphthalen-2(1H)-one;
8-[(5-phenyl-1,3-oxazol-2-yl)amino]-3,4-dihydronaphthalen-2(1H)-one;
8-{[5-(2-methylphenyl)-1,3-oxazol-2-yl]amino}-3,4-dihydronaphthalen-2(1H)-one; and
8-{[5-(3-methylphenyl)-1,3-oxazol-2-yl]amino}-3,4-dihydronaphthalen-2(1H)-one.

18. The compound according to claim 14, wherein
W is —C(R$_x$)(R$_y$);
Y is —C(R$_x$)(R$_y$); and
X is —C(R$_x$)(R$_y$)—C(R$_x$)(R$_y$)—.

19. The compound according to claim 18 wherein R$_x$ is —N(R$_a$)(R$_b$), and R$_a$ and R$_b$ are hydrogen.

20. The compound according to claim 19, wherein the compound is selected from the group consisting of:
N$^1$-(5-p-methylphenyloxazol-2-yl)-5,6,7,8-tetrahydronaphthalene-1,7-diamine;
N$^1$-[5-(4-Trifluoromethylphenyl)oxazol-2-yl]-5,6,7,8-tetrahydronaphthalene-1,7-diamine; and
N$^1$-[5-(2-Fluoro-4-trifluoromethylphenyl)oxazol-2-yl]-5,6,7,8-tetrahydronaphthalene-1,7-diamine.

21. The compound according to claim 18, wherein R$_x$ is selected from the group consisting of hydrogen and —O(R$_a$), wherein R$_y$ is hydrogen, and wherein R$_a$ is hydrogen.

22. The compound according to claim 21, wherein the compound is selected from the group consisting of:
8-({5-[4-(trifluoromethyl)phenyl]-1,3-oxazol-2-yl}amino)-1,2,3,4-tetrahydronaphthalen-2-ol;
8-{[5-(4-tert-butylphenyl)-1,3-oxazol-2-yl]amino}-1,2,3,4-tetrahydronaphthalen-2-ol;
(2S)-8-{[5-(4-tert-butylphenyl)-1,3-oxazol-2-yl]amino}-1,2,3,4-tetrahydronaphthalen-2-ol;
(2R)-8-{[5-(4-tert-butylphenyl)-1,3-oxazol-2-yl]amino}-1,2,3,4-tetrahydronaphthalen-2-ol;
8-{[5-(4-chlorophenyl)-1,3-oxazol-2-yl]amino}-1,2,3,4-tetrahydronaphthalen-2-ol;
8-{[5-(4-pyrrolidin-1-ylphenyl)-1,3-oxazol-2-yl]amino}-1,2,3,4-tetrahydronaphthalen-2-ol;
8-{[5-(4-bromophenyl)-1,3-oxazol-2-yl]amino}-1,2,3,4-tetrahydronaphthalen-2-ol;
8-{[5-(4-methylphenyl)-1,3-oxazol-2-yl]amino}-1,2,3,4-tetrahydronaphthalen-2-ol;
8-{[5-(4-methoxyphenyl)-1,3-oxazol-2-yl]amino}-1,2,3,4-tetrahydronaphthalen-2-ol;
8-[(5-phenyl-1,3-oxazol-2-yl)amino]-1,2,3,4-tetrahydronaphthalen-2-ol;
8-{[5-(2-methylphenyl)-1,3-oxazol-2-yl]amino}-1,2,3,4-tetrahydronaphthalen-2-ol; and 8-{[5-(3-methylphenyl)-1,3-oxazol-2-yl]amino}-1,2,3,4-tetrahydronaphthalen-2-ol.

23. The compound according to claim 18, wherein $R_x$ is —N($R_a$)($R_b$), $R_a$ is —S(O)$_2$(alkyl), and $R_b$ is hydrogen.

24. The compound of claims 23 that is N-[8-(5-p-methylphenyloxazol-2-ylamino)-1,2,3,4-tetrahydronaphthalen-2-yl]methanesulfonamide.

25. The compound according to claim 12, wherein —$R_7$ is cycloalkyl.

26. The compound according to claim 25, wherein
W is —C($R_x$)($R_y$);
Y is —C($R_x$)($R_y$); and
X is —C(O)—C($R_x$)($R_y$)—.

27. The compound according to claim 26, wherein $R_x$ and $R_y$ are hydrogen.

28. The compound according to claim 27, that is 8-{[5-(1-adamantyl)-1,3-oxazol-2-yl]amino}-3,4-dihydronaphthalen-2(1H)-one.

29. The compound according to claim 25, wherein
W is —C($R_x$)($R_y$);
Y is —C($R_x$)($R_y$); and
X is —C($R_x$)($R_y$)—C($R_x$)($R_y$)—.

30. The compound according to claim 29, wherein $R_x$ is selected from the group consisting of hydrogen and —O($R_a$), wherein $R_a$ is hydrogen, and wherein $R_y$ is hydrogen.

31. The compound according to claim 30, that is 8-{[5-(1-adamantyl)-1,3-oxazol-2-yl]amino}-1,2,3,4-tetrahydronaphthalen-2-ol.

32. The compound according to claim 11, wherein $R_2$ is alkyl and $R_1$ is hydrogen.

33. The compound according to claim 32, wherein
W is —C($R_x$)($R_y$);
Y is —C($R_x$)($R_y$); and
X is —C(O)—C($R_x$)($R_y$)—;
and wherein $R_x$ and $R_y$ are hydrogen.

34. The compound according to claim 33, wherein the compound is selected form the group consisting of:
8-[(5-methyl-1,3-oxazol-2-yl)amino]-3,4-dihydronaphthalen-2(1H)-one; and
8-[(5-tert-butyl-1,3-oxazol-2-yl)amino]-3,4-dihydronaphthalen-2(1 h)-one.

35. The compound according to claim 32, wherein
W is —C($R_x$)($R_y$);
Y is —C($R_x$)($R_y$); and
X is —C($R_x$)($R_y$)—C($R_x$)($R_y$)—;
wherein $R_x$ is selected from the group consisting of hydrogen and —O($R_a$),
wherein $R_a$ is hydrogen and wherein $R_y$ is hydrogen.

36. The compound according to claim 35, that is
8-[(5-methyl-1,3-oxazol-2-yl)amino]-1,2,3,4-tetrahydronaphthalen-2-ol; and
8-[(5-tert-butyl-1,3-oxazol-2-yl)amino]-1,2,3,4-tetrahydronaphthalen-2-ol.

37. The compound according to claim 11, wherein $R_2$ is -alkyl-$R_7$ and $R_1$ is hydrogen.

38. The compound according to claim 37, wherein $R_7$ is phenyl.

39. The compound according to claim 38, wherein
W is —C($R_x$)($R_y$);
Y is —C($R_x$)($R_y$);
X is —C(O)—C($R_x$)($R_y$)—; and wherein $R_x$ and $R_y$ are hydrogen.

40. The compound of claim 39 that is 8-[(5-benzyl-1,3-oxazol-2-yl)amino]-3,4-dihydronaphthalen-2(1H)-one.

41. The compound according to claim 38, wherein
W is —C($R_x$)($R_y$);
Y is —C($R_x$)($R_y$);
X is —C($R_x$)($R_y$)—C($R_x$)($R_y$)—;
wherein $R_x$ is selected from the group consisting of hydrogen and —O($R_a$),
wherein $R_a$ is hydrogen and wherein $R_y$ is hydrogen.

42. The compound according to claim 41, wherein the compound is
8-[(5-benzyl-1,3-oxazol-2-yl)amino]-1,2,3,4-tetrahydronaphthalen-2-ol.

43. The compound according to claim 10, wherein
$R_3$ is alkyl;
W is —C($R_x$)($R_y$);
Y is —C($R_x$)($R_y$);
X is —C($R_x$)($R_y$)—C($R_x$)($R_y$)—;
$R_x$ is selected from the group consisting of hydrogen and —O($R_a$), wherein $R_a$ is hydrogen and wherein $R_y$ is hydrogen.

44. The compound according to claim 43, wherein the compound is
8-(methyl{5-[4-(trifluoromethyl)phenyl]-1,3-oxazol-2-yl}amino)-1,2,3,4-tetrahydronaphthalen-2-ol.

45. The compound according to claim 10, wherein
$R_3$ is alkyl;
W is —C($R_x$)($R_y$);
Y is —C($R_x$)($R_y$); and
X is —C(O)—C($R_x$)($R_y$)—.

46. The compound according to claim 10, wherein
$R_3$ is —C(O)alkyl;
W is —C($R_x$)($R_y$);
Y is —C($R_x$)($R_y$);
X is —C($R_x$)($R_y$)—C($R_x$)($R_y$)—;
$R_x$ is selected from the group consisting of hydrogen and —O($R_a$), wherein $R_a$ is hydrogen and wherein $R_y$ is hydrogen.

47. The compound according to claim 46, wherein the compound is
N-[5-(4-tert-butylphenyl)-1,3-oxazol-2-yl]-N-(7-hydroxy-5,6,7,8-tetrahydronaphthalen-1-yl)acetamide.

48. The compound according to claim 10, wherein
$R_3$ is —C(O)alkyl;
W is —C($R_x$)($R_y$);
Y is —C($R_x$)($R_y$); and
X is —C(O)—C($R_x$)($R_y$)—.

49. The compound according to claim 7, wherein
$R_1$ is hydrogen;
$R_2$ is —$R_7$;
$R_3$ is hydrogen;
$R_7$ is phenyl;
W is —C($R_x$)($R_y$);
Y is —C($R_x$)($R_y$);
X is —C($R_x$)($R_y$)—C($R_x$)($R_y$)—;
$R_x$ is —O($R_a$), and $R_y$ is hydrogen.

50. The compound according to claim 49, wherein the compound is:
8-(5-Phenylthiazol-2-ylamino)-1,2,3,4-tetrahydronaphthalen-2-ol.

51. A pharmaceutical composition comprising a therapeutically effective amount of a compound of formula (I) according to claim 1, or a pharmaceutically acceptable salt, ester, or amide thereof.

* * * * *

UNITED STATES PATENT AND TRADEMARK OFFICE
CERTIFICATE OF CORRECTION

PATENT NO. : 7,504,520 B2
APPLICATION NO. : 11/431459
DATED : March 17, 2009
INVENTOR(S) : Arthur Gomtysan et al.

It is certified that error appears in the above-identified patent and that said Letters Patent is hereby corrected as shown below:

Column 2, line 20, "associated with inflammatoary states," to read as --associated with inflammatory states--

Column 5, line 36, "the parent molecula moiety" to read as --the parent molecular moiety--

Column 7, line 8, "and the remainings are carbon." to read as --and the remaining are carbon.--

Column 7, line 62, "is hydrogen Preferred compounds" to read as --is hydrogen. Preferred compounds--

Column 7, line 68, "hydrogen Other compounds comprised are" to read as --hydrogen. Other compounds comprised are--

Column 8, line 5, "hydrogen.and those in which R, is" to read as --hydrogen, and those in which R, is--

Column 8, line 22, "Rx and Ry are hydrogen Other preferred compounds" to read as --Rx and Ry are hydrogen. Other preferred compounds--

Column 10, line 20, "In the case of where reagents of formula" to read as --In the case where reagents of formula--

Column 10, line 24, "Rlo2 is is tert-butoxycarbonyl" to read as --Rlo2 is tert-butoxycarbonyl--

Column 12, line 24, "known as Mitsunobo reaction." to read as --known as Mitsunobu reaction.--

Column 13, line 48, "using Mitsunobo conditions." to read as --using Mitsunobu conditions.--

Column 14, line 42, "phthlimido, can be achieved" to read as --phthalimido, can be achieved--

Column 19, line 21, "alkyl trifilate" to read as --alkyl triflate--

Signed and Sealed this

Tenth Day of August, 2010

David J. Kappos
*Director of the United States Patent and Trademark Office*

CERTIFICATE OF CORRECTION (continued)
U.S. Pat. No. 7,504,520 B2

Column 20, line 27, "The following Examples are intended" to read as --The following examples are intended--

Column 28, line 52, "dihydronaphthalen-2(1 h)-one" to read as --dihydronaphthalen-2(1 H)-one--

Column 35, line 59, "Di-t-butyldicarbonate" to read as --Di-tert-butyldicarbonate--

Column 45, line 42, Claim 34: "3,4-dihydronaphthalen-2(1 h)-one" to read as --3,4-dihydronaphthalen-2(1 H)-one--